US008034576B2

(12) United States Patent
Bricker et al.

(10) Patent No.: US 8,034,576 B2
(45) Date of Patent: Oct. 11, 2011

(54) XANTHURENIC ACID DERIVATIVE PHARMACEUTICAL COMPOSITIONS AND METHODS RELATED THERETO

(75) Inventors: Neal Bricker, Claremont, CA (US); Stewart Shankel, Redlands, CA (US); Christopher D. Cain, Redlands, CA (US); Mark Mitchnick, East Hampton, NY (US); Michael Schmertzler, New Canaan, CT (US)

(73) Assignee: Naturon, Inc., New Canaan, CT (US)

( * ) Notice: Subject to any disclaimer, the term of this patent is extended or adjusted under 35 U.S.C. 154(b) by 0 days.

(21) Appl. No.: 12/642,743

(22) Filed: Dec. 18, 2009

(65) Prior Publication Data

US 2010/0092999 A1 Apr. 15, 2010

Related U.S. Application Data

(63) Continuation of application No. 11/323,580, filed on Dec. 29, 2005, now abandoned, which is a continuation-in-part of application No. 11/027,131, filed on Dec. 29, 2004.

(51) Int. Cl.
*G01N 31/00* (2006.01)
*G01N 33/53* (2006.01)

(52) U.S. Cl. ............ 435/7.21; 435/2; 435/7.1; 436/86; 436/501; 436/518; 514/23; 514/80; 514/454; 514/532

(58) Field of Classification Search ........................ None
See application file for complete search history.

(56) References Cited

U.S. PATENT DOCUMENTS

| 3,817,837 | A | 6/1974 | Rubenstein et al. |
| 4,366,241 | A | 12/1982 | Tom et al. |
| 4,376,110 | A | 3/1983 | David et al. |
| 4,552,884 | A | 11/1985 | Sim et al. |
| 4,559,157 | A | 12/1985 | Smith et al. |
| 4,608,392 | A | 8/1986 | Jacquet et al. |
| 4,620,850 | A | 11/1986 | Bachmann et al. |
| 4,656,188 | A | 4/1987 | Veber et al. |
| 4,938,949 | A | 7/1990 | Borch et al. |
| 4,946,778 | A | 8/1990 | Ladner et al. |
| 4,992,478 | A | 2/1991 | Geria |
| 2003/0152622 | A1 | 8/2003 | Louie-Helm et al. |
| 2004/0157917 | A1 | 8/2004 | Gobaille |
| 2006/0217322 | A1 | 9/2006 | Bricker et al. |

FOREIGN PATENT DOCUMENTS

| GB | 2047691 A | 12/1980 |
| WO | WO-02/15942 | 2/2002 |
| WO | WO-03/005038 | 1/2003 |

OTHER PUBLICATIONS

Ferre et al. Xanthurenic acid 8-O-beta-D-glucoside, a novel tryptophan metabolite in eye-color mutants of *Drosophila melanogaster*. Journal of Biological Chemistry. 260(12): pp. 7509-7514, 1985.*

Shirao et al. Identification of a novel fluorophore, xanthurenic acid 8-O-beta-D-glucoside in human brunescent cataract. Experimental Eye Research. 73: pp. 421-431, 2001.*
Cain et al. Identification of xanthurenic acid 8-O-beta-D-glucoside and xanthurenic acid 8-O-sulfate in human natriuretic hormones. PNAS, 104(45): pp. 17873-17878, Nov. 6, 2007.*
Bricker et al., "Biologic and physical characteristics of the non-peptidic, non-digitalis-like natriuretic hormone", Kidney International, 44: 937-947 (1993).
Buchli et al., Cloning and functional expression of a soluble form of kynurenine/α-aminoadipate aminotransferase from rat kidney, J. Biol. Chem. 270(49): 29330-29335 (1995).
Real and Ferre, "Biosynthesis of xanthurenic acid 8-O-β-D-glucoside in Drosophila", J. Biol. Chem. 265 (13): 7407-7412 (1990).
Cairns and Payne, "The synthesis of 1-alkyl-1,4-dihydro-4-quinoline-2-carboxylic acids", J. Heterocyclic Chem. 15: 551-553 (1978).
Ferre et al., "Xanthurenic acid 8-O-β-D-glucoside, a novel tryptophan metabolite in eye-color mutants of Drosophila melanogaster", J. Biol. Chem., 260(12): 7509-7514 (1985).
Rocchini et al., "Urinary determination of tryptophan and related metabolites through HPLC in reverse phase", Rassegna Chimica 36(1): 15-18 (1984).
Ishiguru et al., "Fluorescent substance in the body of bees", Yakugaku Zasshi 94 (1) 116-23 (1974).
Kotake and Murakami, "A possible diabetogenic role for tryptophan matabolites and effects of xanthurenic acid on insulin", American J. Clinical Nutrition 24 (7): 826-829 (1971). Byran et al., "Mouse bladder carcinogenicity of certain tryptophan metabolites and other aromatic nitrogen compounds suspended in cholesterol", Cancer Research 24 (4): 596-602 (1964).
Misra and Saxena, "Search for potential amoebicides II. synthesis of substituted (sulphazino) quinolines", J. Indian Chem., Soc., 51 (11):967-969 (1974).
Misra et al., "Search for potential amoebicides: II, synthesis of substituted (-sulphazino) quinolines", Acta Ciencia Indica: Chemistry 6 (1) 42-45 (1980).
Real and Ferre, "Distribution of xanthurenic acid glucoside in species of the genus *Drosophila*", Insect Biochemisry 19(2): 111-116 (1989).
Sato et al., "Studies on conjugation of S$^{35}$-sulfate with phenolic compounds", the Journal of Biochemistry (Japan) 49(2): 164-168 (1961).

(Continued)

*Primary Examiner* — Lisa V Cook
(74) *Attorney, Agent, or Firm* — Edwards Angell Palmer & Dodge LLP; Kathleen Williams; Mark D. Russett

(57) ABSTRACT

The present invention relates to diuretic pharmaceutical compositions and methods and in particular to certain derivatives of the formula I:

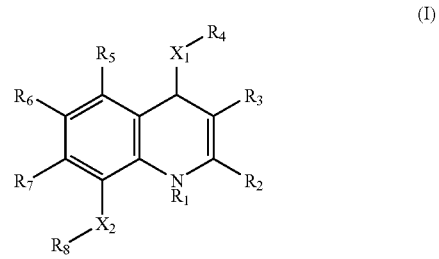

(I)

or a prodrug or pharmaceutically acceptable salt thereof; and
a pharmaceutically acceptable carrier.

6 Claims, 26 Drawing Sheets

OTHER PUBLICATIONS

Sharma et al., "Synthesis and amoebicidal activity of novel substituted quinolines", Indian J. Med. Res. 67: 165-169 (1978).

Shibata et al., "Synthesis of Zeanoside B, a metabolite of IAA in Zea mays L.", Agric. Biol. Chem. 53 (3): 849-850 (1989).

Shirao et al., "Identification of a novel fluorophore, xanthurenic acid 8-O-β-D-glucoside in human brunescent cataract", Exp. Eye Res. 73: 421-431 (2001).

Thiagarajan et al., "Role of xanthurenic acid 8-O-β-D-glucoside, a novel fluorophore that accumulates in the brunescent human eye lens", Photochemistry and Photobiology 76(3): 368- 372 (2002).

Goodman and Gilman's The Pharmacological Basis for Therapeutics, 10$^{th}$ Ed.; Hardman, Limbird & Gilman, Eds. MacGraw-Hill, p. 772, 2001.

Basic and Clinical Immunology, 4$^{th}$ Ed., Chapter 22, "Immunologic Laboratory Tests. Clinical Laboratory Methods for Detection of Antigens and Antibodies" by D. P. Sites et al., published by Lange Medical Publications of Los Altos, Calif., in 1982.

Enzyme Immunoassay, edited by E.T. Maggio, "The EMIT-thyroxine assay"; Enzyme-mulitplied technique (EMIT®) published in 1980 by CRC Press, Inc., Boca Raton, Fla., pp. 141-150, 234-5, and 242-3.

D.S. Smith et al., "A Review of Fluroimmunossay and Immunoflurometric Assay", Ann. Clin. Biochem. (1981) 18:253-274.

Huston et al, "Protein engineering of antibody binding sites: recovery of specific activity in an anti-digoxin single-chain Fv analogue produced in *Escherichia coli*" Proc. Natl. Acad. Sci. USA, 85: 5879-83 (1988).

Ward et al, "Binding activities of a repertoire of a single immunoglobulin variable domains secreted from *Escherichia coli*" Nature, 334: 544-46 (1989).

Köhler and Milstein, "Continuous cultures of fused cells secreting antibody of predefined specificity", Nature, 256: 495-7 (1975).

Kozbor et al., "The production of monoclonal antibodies from human lymphocytes", Immunology Today, 4:72 (1983).

Cote et al., "Generation of human monoclonal antibodies reative with cellular antigens", Proc. Natl. Acad. Sci USA, 80:2026-30 (1983).

Cole et al., "The EBV-hybridoma technique and its application to human lung cancer", in Monoclonal Antibodies and Cancer Therapy, Alan R. Liss, Inc., New York, pp. 77-96 (1985).

Morrison et al, "Chimeric human antibody moleculde: mouse antigen-binding domains with human constant region domains", Proc. Natl. Acad. Sci., 81:6851-6855 (1984).

Huse et al., "Generation of a large combinatorial library of the immunoglobulin repertoire in phage lambda" Science, 246:1275-81 (1989).

Takeda et al, "Construction of chimeric processed immunoglobulin genes containing mouse variable and human constant region sequences", Nature, 314:452-54 (1985).

Voller, "The Enzyme Linked Immunosorbent Assay (ELISA)", Ric Clin Lab, 8:289-98 (1978).

Voller et al., "Enzyme immunoassays with special reference to ELISA techniques", J. Clin. Pathol, 31:507-20 (1978).

Butler, "The amplified ELISA: Principles and applications for the comparative quantitiation of class and subclass antibodies and the distribution of antibodies and antigens in biochemical separates", Meth. Enzymol., 73:482-523 (1981).

Dias et al, "The EMIT Cyclosporine Assay: development of application protocols for the Boehringer Mannheim Hitachi 911 and 917 analyzers", Clin. Biochem. 1997 Mar 30 (2): 15562.

Bird et al., "Single-chain antigen-binding proteins", Science 242:423-26 (1988).

Rich, R.L., et al., "High-resolution and high-throughput protocols for measuring drug/human serum albumin interactions using BIACORE" Analytical Biochemistry, 2001, 296(2): p.197-207.

Marsilio et al., "Simultaneous HPLC determination with light-scattering detection of lactulose and mannitol in studies of intestinal permeability in pediatrics", Clinical Chemistry; 44:16851691 (1998).

He et al., "Analysis of diagnostic metabolites by capillary electrophoresis-mass spectrometry", J Chromatogr B Biomed Sci. Appl. Apr. 30, 1999; 727 (1-2):43-52.

Cain et al., Identification of xanthurenic acid 8-O-beta-D-glucoside and xanthurenic acid 8-O-sulfate as human natriuretic hormones, PNAS 2007, 104(45):17873-17878.

Theodoridis et al., "Solid-phase microextraction for the analysis of biological samples", J Chromatogr B Biomed Sci Appl. Aug. 4, 2000; 745(1) 49-82.

Dorwald F.A., Side Reactions in Organic Synthesis, 2005, Wiley:VCH, Weinheim, pg. IX of preface.

Merck manual, Arterial Hypertension: Merck Manual Professional, http://www.merck.com/mmpe/sec07/ch071/ch071ahtml?qt=diuretics&alt=sh.

* cited by examiner

Na+ Urine Excretion Response to Synthetic Xanthurenic acid 8-O-B-D-glucoside in Normal Sprague Dawley Rat (10.0 ug i.v.)

Na+ Urine Excretion Response to Synthetic Xanthurenic acid 8-O-B-D-glucoside (10 ug, oral administration) followed by Furosemide (100 ug, oral administration) in Normal Sprague Dawley Rat Na+ and K+ Urine Excretion Response to Synthetic Xanthurenic acid 8-O-B-D-glucoside (10 ug, oral administration) followed by furosemide (100 ug, oral administration) in Normal Sprague Dawley Rat Urine Volume Response to Synthetic Xanthurenic acid 8-O-B-D-glucoside (10 ug, oral administration) followed by Furosemide (100 ug, oral administration) in Normal Sprague Dawley Rat Na⁺ Urine Excretion Response to Isolated Xanthurenic acid 8-O-B-D-glucoside (3.0 ug i.v.) followed by Furosemide (20 ug i.v.) in Uremic Sprague Dawley Rat Urine Volume Response to Isolated Xanthurenic acid 8-O-B-D-glucoside (3.0 ug i.v.) followed by Furosemide (20 ug i.v.) in Uremic Sprague Dawley Rat Na⁺ Urine Excretion Response to Isolated Xanthurenic acid 8-sulfate in Uremic Sprague Dawley Rat (2.0 ug i.v.)

Na⁺ and K⁺ Urine Concentration Response to Isolated Xanthurenic acid 8-sulfate in Uremic Sprague Dawley Rat (2.0 ug i.v.)

Na+ and K+ Urine Concentration Response to Synthetic Xanthurenic acid 8-O-sulfate (20 ug oral administration) in Normal Sprague Dawley Rat without Saline Infusion Urine Volume Response to Synthetic Xanthurenic acid 8-O-sulfate (20 ug oral administration) in Normal Sprague Dawley Rat without Saline Infusion Urine Excretion Rate of Normal Sprague Dawley Rat in Response to Furosemide (0.5 mg i.v.)

XANTHURENIC ACID DERIVATIVE PHARMACEUTICAL COMPOSITIONS AND METHODS RELATED THERETO

RELATED APPLICATIONS

The present application is a continuation of U.S. patent application Ser. No. 11/323,580, filed Dec. 29, 2005, which is a continuation-in-part of U.S. application Ser. No. 11/027,131, filed Dec. 29, 2004. The entire contents of each of these applications are incorporated herein by reference.

BACKGROUND OF THE INVENTION

Diuretics are a group of drugs used to treat a variety of medical conditions, including congestive heart failure, hypertension, certain types of liver and kidney diseases and increased intra-ocular pressure. Diuretics act on the transport of sodium ($Na^+$) by the nephrons of the kidney so as to increase the renal excretion of $Na^+$ (and associated ions) and water out of the body and thereby to decrease the extracellular fluid (ECF) volume. Normally, $Na^+$ enters the ECF via the diet, and is excreted in the urine in amounts identical to the intake. In normal adults over 99% of the sodium entering the nephrons of the two kidneys (via glomerular filtration) is transported via an energy dependent process out of the tubular fluid and back into the ECF. When this balance between intake and excretion is upset (with excretion falling below intake) salt retention will occur. A primary mechanism of treating this abnormality involves the administration of one or more agents that reduce $Na^+$ and water reabsorption by the kidneys and thereby increase their excretion in the urine. These agents, collectively, are known as diuretics. Optimally, a powerful diuretic should be natriuretic (inhibit resorption of sodium ions) but not kaliuretic (inhibit resorption of potassium ions) since potassium loss is an undesirable side effect. The principle drugs which are included in the "diuretic" category act by inhibiting the transport of $Na^+$ (and water) out of the tubular fluid by acting on a specific "carrier" in the tubular epithelial cells at a specific site of the nephron. The latter varies with the diuretic employed.

Several major classes of diuretics exist including loop diuretics, thiazide-type diuretics and potassium-sparing diuretics. Loop diuretics, also known as high-ceiling diuretics, act on the thick ascending loop of Henle within the kidney. Examples include furosemide, bumetanide and toresemide. Loop diuretics have a peak diuretic effect far greater than other classes of diuretics. This class acts to inhibit electrolyte reabsorption resulting in the excretion of not only sodium, but also potassium, calcium and magnesium. Loop diuretics are considered "potassium wasting." For example, furosemide is commonly used to treat heart failure, pulmonary edema, hypertension and poisoning. Unfortunately, if dietary potassium is not sufficient, hypokalemia may result and this may induce cardiac arrythmias (Goodman and Gilman's The Pharmacological Basis for Therapeutics, 10th Ed.; Hardman, Limbird & Gilman, Eds. MacGraw-Hill, p. 772, 2001).

Thiazide-type diuretics act in the distal tubule and connecting segment of the kidneys. Examples include chlorothiazide, chlorthalidone, hydrochlorothiazide, indapamide and metolazone. Although thiazides cause less distortion of the electrolyte composition of the extra-cellular fluid than other classes of diuretics, there is also lower intensity of diuresis produced by these drugs. This class contains many sulfonamide chemical entities and thus may cause an allergic reaction in those with sulfa allergies. Although thiazides do not cause calcium excretion, potassium excretion increases with acute administration. Thiazides may also induce hyperglycemia and aggravate pre-existing diabetes mellitus. Thiazide diuretics may also cause increased serum cholesterol, low-density lipoprotein (LDL) and triglyceride concentration. Thiazides are also considered "potassium wasting" diuretics.

Potassium-sparing diuretics may act through either of several mechanisms. Some are steroidal in structure and act in aldosterone-sensitive cells in the cortical connecting tubule in the kidney. Members in this drug class are competitive antagonists of endogenous mineralocorticoid steroids such as aldosterone, which acts to enhance sodium absorption and potassium excretion. The aldosterone receptor is a soluble, cytoplasmic protein found in several tissues including salivary glands, colon and segments of nephrons in the kidney. Spironolactone, a representative member of this drug class, binds to the aldosterone receptor and prevents the receptor from assuming an active conformation. Spironolactone also increases calcium excretion. Common side-effects includes nausea, stomach cramps and diarrhea. Other side effects involve endocrine imbalances, gynecomastia (abnormal enlargement of one or both breasts in men), altered libido, impotence or hirsutism (excessive body hair). Triamterene and amiloride are non-steroidal potassium-sparing diuretics that inhibit electrogenic entry of sodium in the late segments of the kidney nephron. Triamterene and amiloride cause an increase in sodium and chloride excretion, but have little effect on potassium excretion. Side effects of Triamterene include hyperkalemia (increased serum potassium concentration), nausea, vomiting, leg cramps and dizziness. Amiloride side effects also include hyperkalemia, nausea, vomiting, diarrhea and headache.

Other classes of diuretics include osmotic diuretics and carbonic anhydrase inhibitors. Osmotic diuretics, such as mannitol, are poorly reabsorbed by the renal tubules. This drug class effects poor net reabsorption of sodium salts. In addition, mannitol is poorly absorbed by the gastrointestinal tract, and thus must be administered intravenously. Other osmotic diuretics include glycerol, urea and isosorbide.

Carbonic anhydrase inhibitors, such as acetazolamide, cause a modest decrease of sodium reabsorption and may also cause loss of potassium and metabolic acidosis due to its mechanism of action.

Diuretics are used to treat high blood pressure (hypertension), either alone, or in combination with other drugs. High blood pressure adds to the workload of the heart and arteries. If the condition continues for a prolonged period of time, heart and artery function may be impaired. This can damage the blood vessels of the brain, heart and kidneys, resulting in stroke, heart or kidney failure. High blood pressure may also increase the risk of heart attack. These risks can be reduced if blood pressure is properly controlled. The National Heart, Lung, and Blood Institute's (NHLBI) high blood pressure guidelines (JAMA, May 21, 2003) emphasize a need to develop new diuretic medications without the side affects of the aforementioned diuretic pharmacopeia.

SUMMARY OF THE INVENTION

A pharmaceutical composition comprising a therapeutically effective amount of a compound of formula I:

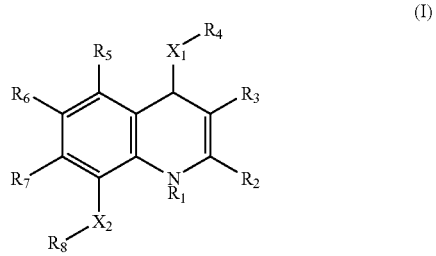

wherein $R_1$, $R_2$, $R_3$, $R_5$, $R_6$ and $R_7$ are independently $X_3R$ where R is selected from the group consisting of H, halo; optionally substituted saccharide, aliphatic, cycloalkyl, heterocycloalkyl, aryl and heteroaryl; —P(O)(OR$^a$)(OR$^b$) and —NR$^a$R$^b$, where R$^a$ and R$^b$ are independently H, optionally substituted aliphatic, cycloalkyl, heterocycloalkyl, aryl or heteroaryl;

$X_1$, $X_2$ and $X_3$ are independently —C(O)O—, —OC(O)—, —C(O)NH—, —NHC(O)—, —OC(O)NH—, —NHC(O)O—, —OS(O)$_y$—, —S(O)$_y$—, —O—, —NHC(O)—, —NHC(O)O—, —S(O)$_2$NH—, a bond or absent; where y is an integer from 0 to 3; and $R_4$ and $R_8$ are independently H, (=O); hydroxy; or optionally substituted saccharide, aliphatic, cycloalkyl, heterocycloalkyl, aryl or heteroaryl; or —P(O)(OR$^a$)(OR$^b$) or —NR$^a$R$^b$, where R$^a$ and R$^b$ are independently H, or optionally substituted aliphatic, cycloalkyl, heterocycloalkyl, aryl or heteroaryl; or a prodrug or pharmaceutically acceptable salt thereof; and a pharmaceutically acceptable carrier.

The present invention also provides methods of treating, controlling and preventing hypertension, edema, acute renal failure, congestive heart failure, chronic renal failure, ascites, increased intra-ocular pressure or nephrotic syndrome and other related diseases and conditions using pharmaceutical compositions comprising compounds of formula I.

A BRIEF DESCRIPTION OF THE DRAWINGS

DETAILED DESCRIPTION OF THE INVENTION

Figure 1:
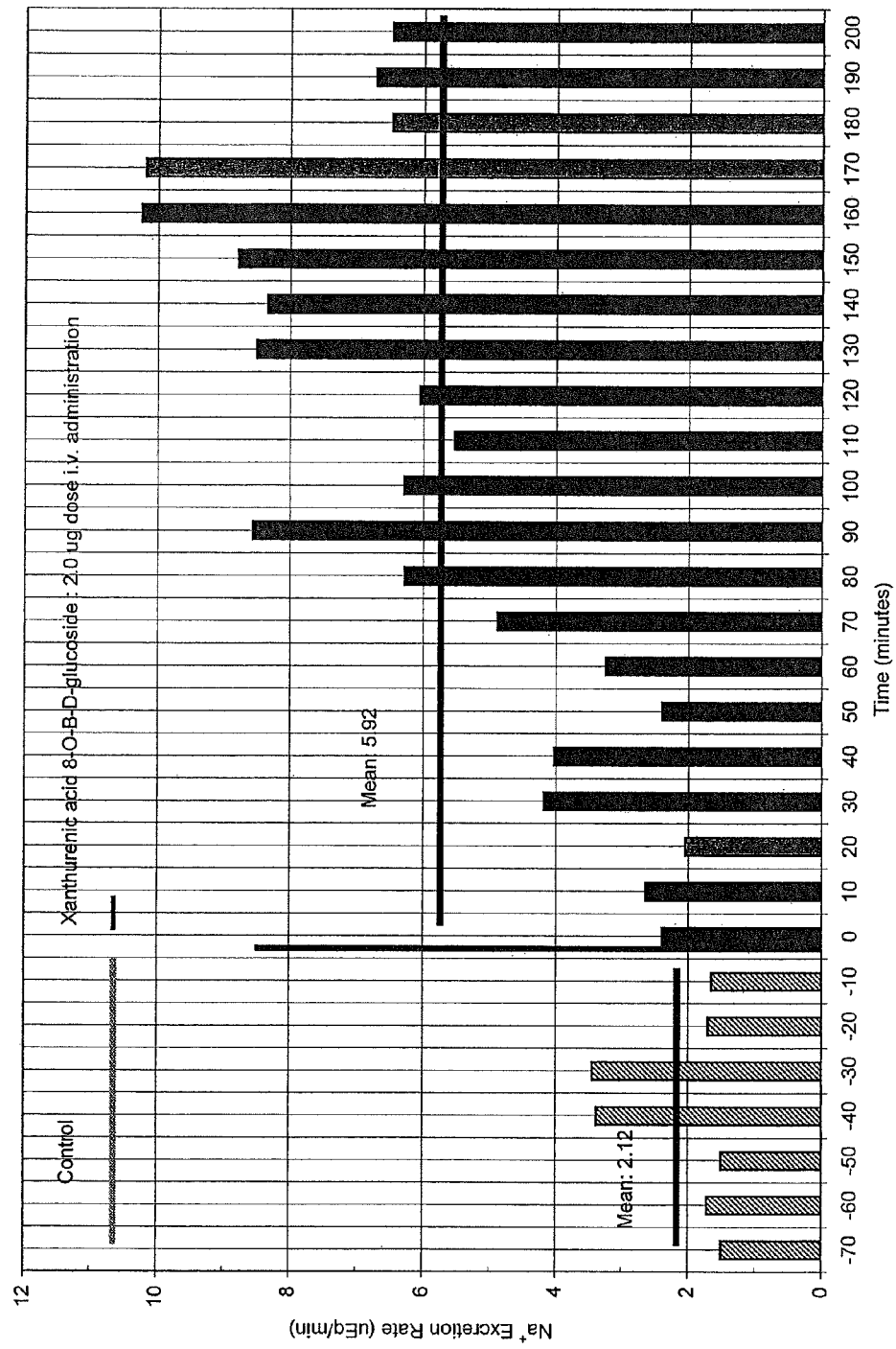
FIG. 1 shows Na$^+$ urine excretion in response to intravenous (i.v.) administration (2 µg dose) of synthetic xanthurenic acid 8-O-β-D-glucoside in a normal Sprague Dawley rat.
Figure 2:
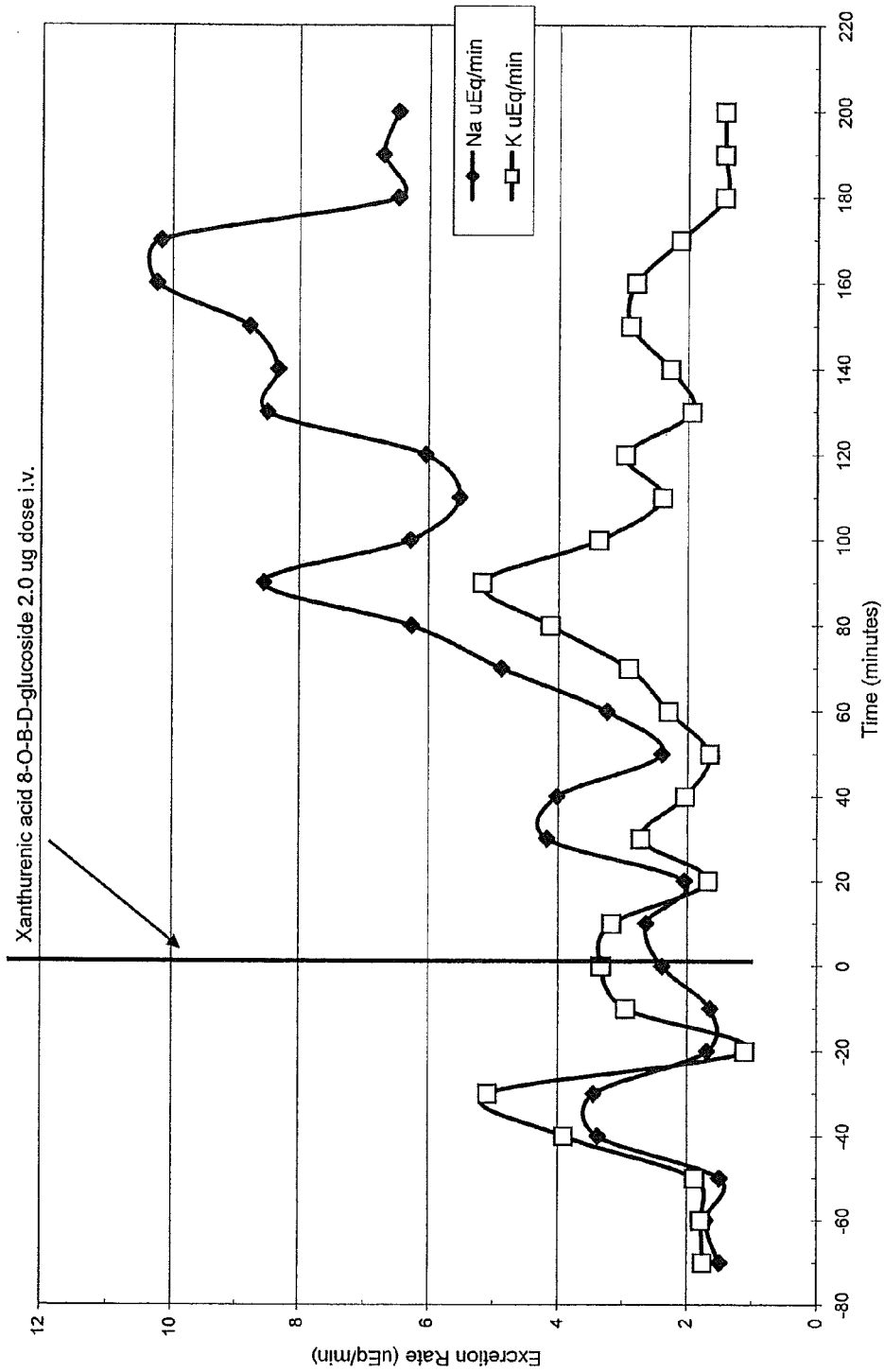
FIG. 2 shows Na$^+$ band K$^+$ urine excretion in response to i.v. administration (2 µg dose) of synthetic xanthurenic acid 8-O-β-D-glucoside in a normal Sprague Dawley rat.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable alkyl groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen. The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on the unsaturated carbon atom of an aryl, heteroaryl, aralkyl or heteroaralkyl group are selected from halogen; haloalkyl; $-CF_3$; $-R^9$; $-OR^9$; $-SR^9$; 1,2-methylenedioxy; 1,2-ethylenedioxy; protected OH (such as acyloxy); phenyl (Ph); Ph substituted with $R^9$; $-O(Ph)$; $-O-(Ph)$ substituted with $R^9$; $-CH_2(Ph)$; $-CH_2(Ph)$ substituted with $R^9$; $-CH_2CH_2(Ph)$; $-CH_2CH_2(Ph)$ substituted with $R^9$; $-NO_2$; $-CN$; $-NR^9R^{10}$; $-NR^9C(O)R^{10}$; $-NR^9C(O)NR^{10}R^{11}$; $-NR^9CO_2R^{10}$; $-NR^9NR^{10}C(O)R^{11}$; $-NR^9-NR^{10}C(O)NR^{11}R^{12}$; $-NR^9NR^{10}CO_2R^{11}$; $-C(O)C(O)R^9$; $-C(O)CH_2C(O)R^9$; $-CO_2R^9$; $-C(O)R^9$; $-C(O)NR^9R^{10}$; $-OC(O)NR^9R^{10}$; $-S(O)_2R^9$; $-SO_2NR^9R^{10}$; $-S(O)R^9$; $-NR^9SO_2NR^{10}R^{11}$; $-NR^9SO_2R^{10}$; $-C(=S)NR^9R^{10}$; $-C(=NH)-NR^9R^{10}$; $-(CH_2)_yNHC(O)R^9$; $-(CH_2)_yR^9$; $-(CH_2)_yNHC(O)NHR^9$; $-(CH_2)_yNHC(O)OR^9$; $-(CH_2)_yNHS(O)R^9$; $-(CH_2)_yNHSO_2R^9$ or $-(CH_2)_yNHC(O)CH((V)_z-R^9)(R^{10})$ wherein $R^9$, $R^{10}$, $R^{11}$ and $R^{12}$ are independently selected from hydrogen, optionally substituted $C_{1-6}$ aliphatic, an unsubstituted 5-6 membered heteroaryl or heterocyclic ring, phenyl (Ph), $-O(Ph)$ or $-CH_2(Ph)-CH_2(Ph)$, wherein y is 0-6; z is 0-1; and V is a linker group. When $R^9$, $R^{10}$, $R^{11}$ or $R^{12}$ is $C_{1-6}$ aliphatic, it may be substituted with one or more substituents selected from $-NH_2$, $-NH(C_{1-4}$ aliphatic), $-N(C_{1-4}$ aliphatic)$_2$, $-S(O)(C_{1-4}$ aliphatic), $-SO_2(C_{1-4}$ aliphatic), halogen, $(C_{1-4}$ aliphatic), $-OH$, $-O-(C_{1-4}$ aliphatic), $-NO_2$, $-CN$, $-CO_2H$, $-CO_2(C_{1-4}$ aliphatic), $-O$(halo $C_{1-4}$ aliphatic), or $-$halo($C_{1-4}$ aliphatic); wherein each $C_{1-4}$ aliphatic is unsubstituted.

An aliphatic group or a non-aromatic heterocyclic ring may contain one or more substituents. Suitable substituents on the saturated carbon of an alkyl group or of a non-aromatic heterocyclic ring are selected from those listed above for the unsaturated carbon of an aryl or heteroaryl group and the following: $=O$, $=S$, $=NNHR^{13}$, $=NNR^{13}R^{14}$, $=N-$, $=NNHC(O)R^{13}$, $=NNHCO_2(alkyl)$, $=NNHSO_2(alkyl)$, or $=NR^{13}$, where $R^{13}$ and $R^{14}$ are independently selected from hydrogen and an optionally substituted $C_{1-6}$ aliphatic. When $R^{13}$ or $R^{14}$ is $C_{1-6}$ aliphatic, it may be substituted with one or more substituents selected from $-NH_2$, $-NH(C_{1-4}$ aliphatic), $-N(C_{1-4}$ aliphatic)$_2$, halogen, $-OH$, $-O-(C_{1-4}$ aliphatic), $-NO_2$, $-CN$, $-CO_2H$, $-CO_2(C_{1-4}$ aliphatic), $-O$(halo $C_{1-4}$ aliphatic) or -halo($C_{1-4}$ aliphatic); wherein each $C_{1-4}$ aliphatic is unsubstituted.

Substituents on the nitrogen of a non-aromatic heterocyclic ring are selected from $-R^{15}$, $-NR^{15}R^{16}$, $-C(O)R^{15}$, $-CO_2R^{15}$, $-C(O)C(O)R^{15}$, $-C(O)CH_2C(O)R^{15}$, $-SO_2R^{15}$, $-SO_2NR^{15}R^{16}$, $-C(=S)NR^{15}R^{16}$, $-C(=NH)NR^{15}R^{16}$ or $-NR^{15}SO_2R^{16}$; wherein $R^{15}$ and $R^{16}$ are independently selected from hydrogen, an optionally substituted $C_{1-6}$ aliphatic, optionally substituted phenyl (Ph), optionally substituted —O(Ph), optionally substituted —$CH_2$(Ph), optionally substituted —$CH_2CH_2$(Ph), or an unsubstituted 5-6 membered heteroaryl or heterocyclic ring. When $R^{15}$ or $R^{16}$ is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2H$, —$CO_2$($C_{1-4}$ aliphatic), —O(halo $C_{1-4}$ aliphatic) or -halo($C_{1-4}$ aliphatic); wherein each $C_{1-4}$ aliphatic is unsubstituted.

The term "saccharide" defines a carbohydrate, or sugar, made up of one or more units with the empirical generic formula ($CH_2O$). A saccharide is further classified as a monosaccharide, disaccharide or polysaccharide depending on the number of units or an aminosaccharide if one or more oxygen atoms are replaced by a nitrogen atom. A saccharide may also be classified as a deoxysaccharide if one or more hydroxy groups are replaced by a hydrogen atom.

A saccharide substituent may be further substituted on any primary or secondary hydroxy group by, for example, an alkyl, alkoxyalkyl, aryl, heteroaryl, ether, ester, acetal, carbonate or carbamate.

The term "monosaccharide" defines a single carbohydrate, or sugar unit. Two families of monosaccharides are aldoses or ketoses. Aldoses have a carbonyl group at the end of the carbon chain as an aldehyde, when the monosaccharide is written in a linear, open-chain formula. If the carbonyl is in any other position in the carbon chain the monosaccharide is a ketone and referred to as a ketose. Three carbon monosaccharides are trioses: glyceraldehydes, an aldose, and dihydroxyacetone, a ketose. Monosaccharides, except for dihydroxyacetone, have one or more asymmetric centers. The prefixes D- or L-refer to the configuration of the carbon atom of the chiral carbon most distant from the carbonyl carbon. Monosaccharides with 4, 5, 6 and 7 carbon atoms in their backbones are termed tetroses, pentoses, hexoses, and heptoses, respectively. Each of these exists in two series: aldotetroses and ketotetroses, aldopentoses and ketopentoses, aldohexoses and ketohexoses, aldoheptoses and ketoheptoses. Tetroses include erythrose and threose. Pentoses include ribose, arabinose, xylose and lyxose. Hexoses include allose, altrose, glucose, mannose, gulose, idose, galactose and talose. Monosaccharides with 5 or more carbons in the backbone usually occur as cyclic, or ring, structures in which the carbonyl carbon has formed a covalent bond with one of the hydroxy groups along the chain. Six-membered ring compounds are termed pyranoses, five-membered ring compounds are furanoses. Formation of a six-membered ring results from reaction of aldehydes and alcohols to form hemiacetals which contain an asymmetric carbon atom. One configuration around the C-1 carbon is described as α- and the other is described as the β-form.

The term "disaccharide" refers to a molecular moiety containing two monosaccharides covalently bound to each other. Disaccharides include maltose [glucose-glucose], lactose [galactose-glucose] and sucrose [fructose-glucose].

The term "polysaccharide" includes multiple monosaccharides units covalently bound to each other. Polysaccharides include starch, hyaluronic acid, amylose, amylopectin, dextran, cyclodextrin and glycogen.

The term "aminosaccharide" refers to a carbohydrate molecule where one or more hydroxy groups are replaced by an amino group. This includes the monosaccharides glucosamine and muramic acid and the polysaccharide chitin. The amino groups may be acetylated to include N-acetyl-D-glucosamine and N-acetyl-D-muramic acid.

The term "deoxysaccharide" refers to a carbohydrate molecule where one or more hydroxy groups are replaced by hydrogen. These include, for example, L-rhamnose (6-deoxy-L-mannose), L-fucose (6-deoxy-L-galactose) and D-fucose (rhodeose).

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts) of the compounds of the invention. Pharmaceutically acceptable salts of compounds of formula I are where, for example, an exchangeable group, such as hydrogen in —OH or —NH— is replaced with a pharmaceutically acceptable cation (e.g. a sodium, potassium, or ammonium ion) and can be conveniently be prepared from a corresponding compound of formula I by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "disease," "disorder" or "condition" as used herein, means any disease or other deleterious condition or disease in which therapeutic administration of a diuretic drug, or pharmaceutical composition, is known to play a role in treatment thereof. Such diseases or conditions include, without limitation, hypertension, edema, acute renal failure, congestive heart failure, chronic renal failure, ascites, intra-ocular pressure or nephrotic syndrome and complications due to or exacerbated by those conditions.

The term "diuretic" as used herein, means a drug or other substance tending to promote the formation and excretion of urine.

The term "hypertension" as used herein, refers to a disorder characterized by elevated blood pressure.

"Antibody" refers to a member of a family of glycosylated proteins called immunoglobulins, which can specifically combine with an antigen.

"Antigen" refers to a compound which will give rise to antibody formation.

"Antigenic determinant" or "antigenic determinant site" refers to the actual site of antibody recognition of the antigen. The term is used interchangeably with "epitope".

"Carrier" refers to a high molecular weight (macromolecular) polymeric material, usually a protein, to which an antigen or hapten can be bound or conjugated so as to facilitate antibody formation. Carriers can incorporate labels in their structure, if desired.

"Conjugate" refers to an antigen or hapten chemically bonded to a carrier; a conjugate can contain other groups, as well.

"ELISA" refers to an enzyme-linked immunosorbent assay which employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of Basic and Clinical Immunology by D. P. Sites et al, published by Lange Medical Publications of Los Altos, Calif., in 1982, which is incorporated herein by reference.

"EMIT" refers to an enzyme-multiplied immunoassay technique which uses (1) an enzyme-labeled hapten, (2) specific antibody to the hapten, (3) pretreatment reagent, (4) buffered-enzyme substrate, and (5) standards to detect the amount of an unknown in a sample. A description of the EMIT technique is found in Enzyme Immunoassay, edited by E. T. Maggio, published in 1980 by CRC Press, Inc., Boca Raton, Fla., particularly on pp. 141-150, 234-5, and 242-3. These materials are incorporated by reference.

"Epitope" refers to that portion of a molecule which is specifically recognized by an antibody. It is also referred to as a determinant.

"Fluoroimmunoassay" refers to an antibody-based assay in which the species to be measured binds to, displaces or competes for binding with a material labelled with a fluorescent species in an antibody-ligand complex. In some embodiments of this assay, the complex is separated and the presence or absence of fluorescent species gives a measure of the amount of measured species. In other embodiments, the complex has different fluorescent properties than the uncomplexed fluorescent species so that the formation of the complex can be detected without separation of the complex. A description of fluoroimmunoassay techniques is found in "A Review of Fluoroimmunoassay and Immunofluorometric Assay", D. S. Smith et al. (1981) Ann. Clin. Biochem. (1981) 18; 253-274 which is incorporated herein by reference.

"Hapten" refers to a compound, usually of low molecular weight, which when bound to a larger molecule can give rise to antibody formation.

"Label" refers to a detectable group in a molecule. Among the common labels are radioactive species useful in radioimmunoassays, fluorescent species useful in fluoroimmunoassays, and enzymatic species useful in the ELISA and EMIT methods and the like.

"Ligand" refers to any molecule which has an antibody combining site and can bind to a receptor.

"Standard" refers to a sample of a specific molecule present in a known concentration used to quantitate the same specific molecule in an unknown concentration of a different sample.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of hydrogen by a deuterium or tritium, or the replacement of a carbon by a $^{13}C$— or $^{14}C$-enriched carbon are within the scope of this invention.

One aspect of the present invention relates to pharmaceutical compositions comprising compounds of formula I. In one preferred embodiment, the composition comprises compounds of formula I wherein $R_1$, $R_3$, $R_5$, $R_6$ and $R_7$ are independently H, halogen or lower alkyl. In another, $X_1$ is absent and $R_4$ is (=O); or $X_1$ is a bond and $R_4$ is hydroxy. In another embodiment, $X_1R_4$ is —OC(O)CH$_3$. In another embodiment, $R_2$ is —C(O)OR where R is preferably H or optionally substituted alkyl where alkyl may be methyl, ethyl, butyl, octyl or undecyl. In another embodiment, $R_2$ is —C(O)NHR where R is preferably H or optionally substituted alkyl, cycolalkyl, heterocycloalkyl, aryl or heteroaryl.

In one embodiment of the invention, $X_2$ is —O— and $R_8$ is an optionally substituted saccharide, preferably a monosaccharide selected from an aldohexopyranose, aldopentopyranose, aldopentofuranose or ketose. In other embodiments, $R_8$ is D-galactose, D-mannose, D-ribose, D-fucose or L-rhamnose. In a preferred embodiment, $R_8$ is D-glucose. In one specific embodiment, the compound of formula I is xanthurenic acid 8-O-β-D-glucoside.

In another embodiment, $X_2$ is —O— and $R_8$ is —CH$_2$CO$_2$R or —CH$_2$C(O)NHR where R is preferably H or optionally substituted alkyl, cycolalkyl, heterocycloalkyl, aryl or heteroaryl.

According to another embodiment of the invention, the pharmaceutical composition comprises a compound of formula I where $X_2R_8$ is an acyl, phosphate, phosphonic acid, alkyl phosphonate or a sulfate group. In one specific embodiment, the compound is xanthurenic acid 8-O-sulfate.

The invention further provides a pharmaceutical composition comprising a therapeutically effective amount of a compound represented by formula I in combination one or more additional diuretic compounds or cardiovascular agents; and a pharmaceutically acceptable carrier.

The pharmaceutical compositions described herein are useful for treatment or prevention of hypertension, edema, acute renal failure, congestive heart failure, chronic renal failure, ascites, intra-ocular pressure or nephrotic syndrome and complications due to or exacerbated by those conditions.

Depending upon the particular condition to be treated or prevented, additional therapeutic agents, which are normally administered to treat or prevent that condition, may be administered together with the compounds of this invention. For example, in the treatment of hypertension, one or more additional diuretic compounds or cardiovascular agents may be combined with the compounds of this invention to treat hypertension. The additional diuretic agent is selected from the group consisting of a loop diuretic, thiazide diuretic, potassium-sparing diuretic, carbonic anhydrase inhibitor and osmotic diuretic. The cardiovascular agent is selected from the group consisting of an angiotensin converting enzyme inhibitor, angiotensin II receptor antagonist, beta-adrenergic blocker, calcium channel blocker, cholesterol altering drug, triglyceride lowering agent, c-reactive protein lowering agent, homocysteine lowering agent, aspirin and its derivatives, ionotropic agent, antiarrhythmic agent and blood thinner (anticoagulant). These agents include, without limitation, furosemide, bumetanide, torsemide, ethacrynic acid, chlorothiazide, hydrochlorothiazide, spironolactone, amiloride, triamterene, acetazolamide, methazolamide, dichlorphenamide, hydroflumethiazide, methyclothiazide, indapamide, metolazone, polythiazide, chlorthalidone, dorzolamide, brinzolamide, glycerol, mannose, urea, lisinopril, moexipril, enalapril, irbesartan, valsartan, losartan, nadolol, propranolol, atenolol, timolol and bisoprolol.

The compounds of formula I can be formulated as pharmaceutical compositions and administered to a mammalian host, such as a human patient, in a variety of forms adapted to a selected route of administration, i.e., by oral, parenteral, intravenous, intramuscular, topical, or subcutaneous routes. Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc.

Topical applications may be formulated in hydrophobic or hydrophilic bases as ointments, creams, lotions, paints, powders, etc.

For veterinary medicine, the composition may, for example, be formulated as an intra-mammary preparation in either long acting or quick-release bases.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The compositions per unit dosage, whether liquid or solid may contain from 0.1% to 99% of active material (compound I or salts thereof), the preferred range being from about 10-60%. The composition will generally contain from about 15 mg to about 1,500 mg by weight of active ingredient based upon the total weight of the composition; however, in general, it is preferable to employ a dosage amount in the range of from about 250 mg to 1,000 mg. In parenteral administration the unit dosage is usually the pure compound in a slightly acidified sterile water solution or in the form of a soluble powder intended for solution. Single dosages for injection, infusion or ingestion may be administered, i.e., 1-3 times daily, to yield levels of about 0.5-50 mg/kg, for adults.

Production of Antibodies

The present disclosure further includes methods for the production of antibodies capable of specifically recognizing xanthurenic acid-8-O-β-D-glucoside. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of xanthurenic acid-8-O-β-D-glucoside in a biological sample, or, alternatively, as a method for the inhibition of abnormal xanthurenic acid-8-O-β-D-glucoside activity. Thus, such antibodies may be utilized as part of disease treatment methods, and/or may be used as part of diagnostic techniques whereby patients may be tested for abnormal levels of xanthurenic acid-8-O-β-D-glucoside.

For the production of antibodies, conjugates of xanthurenic acid-8-O-β-D-glucoside with, for example, a carrier protein such as KLH or ovalbumin, may be generated by activation of the xanthurenic acid-8-O-β-D-glucoside carboxyl group with, for example, a water soluble carbodiimide, such as EDC, to form a xanthurenic acid-8-O-β-D-glucoside bioconjugate immunogen. Various host animals may be immunized by injection with the xanthurenic acid-8-O-β-D-glucoside bioconjugate immunogen in, for example, an adjuvanted protocol. Such host animals include rabbits, mice, rats, goats and chickens, and the like. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as xanthurenic acid-8-O-β-D-glucoside bioconjugate immunogen. For the production of polyclonal antibodies, host animals such as those described above, may be immunized by injection with xanthurenic acid-8-O-β-D-glucoside bioconjugate immunogen supplemented with adjuvants as also described above.

Methods for generating polyclonal antibodies to antigens using host animals are known generally to the art. In a typical preparation, one or more of the xanthurenic acid-8-O-β-D-glucoside bioconjugate immunogens is introduced into a mammalian or avian host. Suitable hosts include, for example, monkeys, cattle, rabbits, rats, mice, and the like. This is usually accomplished by subcutaneous injection as a solution in saline which has been emulsified with, for example, complete Freund's adjuvant. Animal antibody titers may be followed by ELISA. After several weeks, a boost of xanthurenic acid-8-O-β-D-glucoside bioconjugate immunogen in, for example, Freund's incomplete adjuvant, may serve to increase the antibody titer. The antibodies are collected by bleeding the animal after about a month. The whole blood is allowed to clot at 25.degree. C. for several hours. Aqueous ammonium sulfate solution is added to achieve 40% by weight of aqueous solution, and the IgG fraction precipitates. The precipitate is collected by centrifugation and resuspended in saline or buffer solution to the desired concentration.

The purified antibody fraction may be further modified for use in diagnostic assay systems. Such modification may encompass linkage with enzymes such as lipozyme, lactoperoxidase, alkaline phosphatase and others for use in ELISA assays. The antibody may be modified with fluorescent moieties. Optimally, this fluorescence may be quenched or enhanced upon binding of the antibody and antigen. These techniques for assaying the extent of the antibody-antigen interaction are known in the art. The xanthurenic acid-8-O-β-D-glucoside, xanthurenic acid-8-O-β-D-glucoside conjugates and antibodies of this disclosure are also useful in the detection and diagnosis of various sodium imbalance disorders, particularly in providing high purity materials useful for calibration solutions for assay techniques, such as ELISA or EMIT.

Monoclonal antibodies, which are homogeneous populations of antibodies to a particular antigen, may be obtained by any technique that provides for the production of antibody molecules by continuous cell lines in culture. These include, but are not limited to the hybridoma technique of Köhler and Milstein, *Nature*, 256:495-7 (1975); and U.S. Pat. No. 4,376, 110), the human B-cell hybridoma technique (Kosbor et al., *Immunology Today*, 4:72 (1983); Cote et al., *Proc. Natl. Acad Sci. USA*, 80:2026-30 (1983)), and the EBV-hybridoma technique (Cole et al., in Monoclonal Antibodies And Cancer Therapy, Alan R. Liss, Inc., New York, pp. 77-96 (1985)). Such antibodies may be of any immunoglobulin class including IgG, IgM, IgE, IgA, IgD and any subclass thereof. The hybridoma producing the mAb of this disclosure may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci.*, 81:6851-6855 (1984); Takeda et al., *Nature*, 314:452-54 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423-26 (1988); Huston et al., *Proc. Natl. Acad. Sci. USA,* 85:5879-83 (1988); and Ward et al., *Nature,* 334:544-46 (1989)) can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries may be constructed (Huse et al., *Science,* 246:1275-81 (1989)) to allow rapid and easy identification of monoclonal Fab fragments with the desired specificity.

The enzymes for use in the diagnostic reagents, standards or kits can vary widely, depending on the ease of conjugation, turnover rate, and the physiological fluid in which the unknown (analyte) is to be measured. Representative enzymes of choice include hydrolysases, nucleases, amidases, esterases and the like which are found in U.S. Pat. No. 3,817,837, which is incorporated herein by reference.

The methods and apparatus for labeling an antibody as described herein for use in a diagnostic reagent, standard or kit is found in U.S. Pat. No. 4,366,241, which is incorporated herein by reference.

Diagnostics

The present invention further includes the quantitation of xanthurenic acid-8-O-β-D-glucoside in human fluids (whole blood, urine, csf, serum, plasma, ocular, feces, sweat) which may be used to correlate to a disorder of sodium imbalance. Such disorders may include hypertension (low renin, low angiotensin), congestive heart failure (edema), nephrotic syndrome, cirrhosis of the liver, premenstrual edema, cyclical edema, and cardiogenic shock. Other clinical conditions in which xanthurenic acid-8-O-β-D-glucoside quantitation may prove useful include post-operative settings, and battlefield settings, where the patient is given too much fluid; and potassium-sparing in conjunction with furosemide administration. Xanthurenic acid-8-O-β-D-glucoside quantitation may also be useful in "Escape Syndrome" where a tumor inappropriately increases, affecting aldosterone; then sodium excretion decreases causing increase of fluid retention by two liters in the cardiovascular system. At this point, "escape" occurs by causing fluid and sodium loss and thus maintaining an overloaded state of two liters. It is proposed that the overloaded fluid state causes an increase in xanthurenic acid-8-O-β-D-glucoside, which in turn causes "escape" by stimulating sodium excretion and concomitant fluid loss.

A variety of methods may be employed to diagnose disease conditions associated with an excess or a deficiency of xanthurenic acid-8-O-β-D-glucoside.

The methods described herein may be performed, for example, by utilizing pre-packaged diagnostic kits comprising at least one specific antibody reagent described herein, which may be conveniently used, e.g., in clinical settings, to diagnose patients exhibiting disease symptoms or at risk for developing disease.

Any human biological sample or tissue may be utilized in the diagnostics described below. For example, whole blood, urine, saliva, cerebral spinal fluid, serum, plasma, ocular, feces or sweat may be utilized.

Diagnostic methods for the detection of xanthurenic acid-8-O-β-D-glucoside in biological samples may involve, for example, immunoassays such as heterogeneous enzyme immunoassays which include solid phase enzyme-linked immunosorbent assays (ELISA); and solution phase homogeneous enzyme immunoassays which include enzyme-multiplied immunoassay technique (EMIT). Xanthurenic acid-8-O-β-D-glucoside may be measured by high pressure liquid chomatography (HPLC), capillary electrophoresis (CE), or capillary electrophoresis-mass spectrometry (CE-MS) with optional pretreatment of, for example, a urine sample by solid phase extraction. Further, surface plasmon resonance (SPR) techniques may be developed in which a chip-based optical biosensor system is used to investigate the functional nature of xanthurenic acid-8-O-β-D-glucoside binding to target membrane molecules in which the source of xanthurenic acid-8-O-β-D-glucoside is from an impure mixture, such as serum, urine, and cell culture media. SPR techniques will be useful in finding and characterizing membrane receptors for xanthurenic acid-8-O-β-D-glucoside in different cells types.

Immunoassays for xanthurenic acid-8-O-β-D-glucoside typically comprise incubating a biological sample, such as a biological fluid, a tissue extract, freshly harvested cells, or cells that have been incubated in tissue culture, in the presence of a detectably labeled antibody capable of identifying xanthurenic acid-8-O-β-D-glucoside, and detecting the bound antibody by any of a number of techniques well known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene-specific antibody. The solid phase support may then be washed with the buffer a second time to remove unbound antibody. The amount of bound label on solid support may then be detected by conventional means.

The terms "solid phase support or carrier" are intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

In practice, microtiter plates are conveniently utilized for many immunoassays. The anchored component may be immobilized by non-covalent or covalent attachments. Non-covalent attachment may be accomplished simply by coating the solid surface with a solution of a xanthurenic acid-8-O-β-D-glucoside bioconjugate and drying. Alternatively, an immobilized antibody, preferably a monoclonal antibody, specific for xanthurenic acid-8-O-β-D-glucoside may be used to anchor the protein to the solid surface. The surfaces may be prepared in advance and stored. In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

For example, competitive inhibition assays are often used to measure small analytes, such as xanthurenic acid-8-O-β-D-glucoside, because competitive inhibition assays only require the binding of one antibody rather than two as is used in standard ELISA formats. Because of the probability for steric hindrance occurring when two antibodies attempt to bind to a small molecule at the same time, a sandwich assay format may not be feasible, therefore a competitive inhibition assay may be preferable. In a sequential competitive inhibition assay, the sample and conjugated analyte are added in steps like a sandwich assay, while in a classic competitive inhibition assay, these reagents are incubated together at the same time.

In a sequential competitive inhibition assay format, a monoclonal antibody (MAb) is coated onto a 96-well microtiter plate. When the sample is added, the MAb captures free analyte out of the sample. In the next step, a known amount of analyte labeled with either biotin or HRP is added. The labeled analyte will then also attempt to bind to the MAb adsorbed onto the plate, however, the labeled analyte is inhibited from binding to the MAb by the presence of previously bound analyte from the sample. This means that the labeled analyte will not be bound by the monoclonal on the plate if the monoclonal has already bound unlabeled analyte from the sample. The amount of unlabeled analyte in the sample is inversely proportional to the signal generated by the labeled analyte. The lower the signal, the more unlabeled analyte there is in the sample. A standard curve can be constructed using serial dilutions of an unlabeled analyte standard. Subsequent sample values can then be read off the standard curve as is done in the sandwich ELISA formats.

The classic competitive inhibition assay format requires the simultaneous addition of labeled (conjugated analyte) and unlabeled analyte (from the sample). Both labeled and unlabeled analyte then compete simultaneously for the binding site on the monoclonal capture antibody on the plate. Like the sequential competitive inhibition format, the colored signal is inversely proportional to the concentration of unlabeled target analyte in the sample.

Detection of labeled analyte may be made by using a peroxidase substrate such as TMB, which can be read on a microtiter plate reader. For example, with a standard curve (1 blank and 7 standards) and 3 controls, a 96-well microtiter plate format can test 21 samples in triplicate and 37 samples in duplicate.

As another example, antibodies, or fragments of antibodies useful in the present disclosure may be used to quantitatively or qualitatively detect the presence of xanthurenic acid-8-O-β-D-glucoside. This can be accomplished, for example, by immunofluorescence techniques employing a fluorescently labeled antibody (see below) coupled with light microscopic, flow cytometric, or fluorimetric detection.

The antibodies (or fragments thereof) useful in the present disclosure may, additionally, be employed histologically, as in immunofluorescence or immunoelectron microscopy, for in situ detection of xanthurenic acid-8-O-β-D-glucoside. In situ detection may be accomplished by removing a histological specimen from a patient, and applying thereto a labeled antibody of the present disclosure. The antibody (or fragment) is preferably applied by overlaying the labeled antibody (or fragment) onto a biological sample. Through the use of such a procedure, it is possible to determine not only the presence of the xanthurenic acid-8-O-β-D-glucoside, but also their distribution in the examined tissue. Using the present disclosure, those of ordinary skill will readily perceive that any of a wide variety of histological methods (such as staining procedures) can be modified in order to achieve such in situ detection.

Those skilled in the art will be able to determine operative and optimal assay conditions for each determination by employing routine experimentation.

One of the ways in which the gene peptide-specific antibody can be detectably labeled is by linking the same to an enzyme and using it in an enzyme immunoassay (EIA) (Voller, *Ric Clin Lab*, 8:289-98 (1978) ["The Enzyme Linked Immunosorbent Assay (ELISA)", Diagnostic Horizons 2:1-7, 1978, Microbiological Associates Quarterly Publication, Walkersville, Md.]; Voller et al., *J. Clin. Pathol.*, 31:507-20 (1978); Butler, *Meth. Enzymol.*, 73:482-523 (1981); Maggio (ed.), Enzyme Immunoassay, CRC Press, Boca Raton, Fla. (1980); Ishikawa et al., (eds.) Enzyme Immunoassay, Igaku-Shoin, Tokyo (1981)). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect xanthurenic acid-8-O-β-D-glucoside through the use of a radioimmunoassay (RIA) (see, e.g., Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediamine-tetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present disclosure. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Throughout this application, various publications, patents and published patent applications are referred to by an identifying citation. The disclosures of these publications, patents and published patent specifications referenced in this application are hereby incorporated by reference into the present disclosure to more fully describe the state of the art to which this disclosure pertains.

Enzyme-multiplied immunoassay techniques (EMIT) may be employed due to the small size of xanthurenic acid-8-O-β-D-glucoside. Various EMIT methods could be used in both qualitative and quantitative assays by, for example, the methods described by Dias, et al. (see Dias et al., "The EMIT Cyclosporine Assay: development of application protocols for the Boehringer Mannheim Hitachi 911 and 917 analyzers" Clin. Biochem. 1997 March; 30(2):155-62). Advantages of EMIT in the clinical setting include (1) minimal or no sample preparation, (2) small sample size, (3) excellent correlation with other methods such as HPLC and RIA, (4) rapid time since there is no need for separation of free and bound enzyme labels (less than one minute), ease of adaptation to most general chemistry analyzers.

Surface plasmon resonance (SPR) may also be employed to detect xanthurenic acid-8-O-β-D-glucoside as a solution phase interactant to immobilized xanthurenic acid-8-O-β-D-glucoside specific antibody. The techniques of McDonnell and of Rich et al. may be employed for the SPR methods development (McDonnell, J. M., "Surface plasmon resonance: towards an understanding of the mechanisms of biological molecular recognition. Current Opinion in Chemical Biology, 2001. 5(5): p. 572-577; Rich, R. L., et al., "High-resolution and high-throughput protocols for measuring drug/human serum albumin interactions using BIACORE" Analytical Biochemistry, 2001. 296(2): p. 197-207). Various flow-through cells may be constructed and placed in-line with commercially available SPR biosensing instruments, such as those with trademark Biocore. In general, the specific antibody may be immobilized on an SPR-active gold-coated glass slide which forms one wall of a flow-cell; and the analyte xanthurenic acid-8-O-β-D-glucoside in an aqueous buffer solution is injected to flow across the flow-cell. When light (visible or near infrared) is shined through the glass slide and onto the gold suface at angles and wavelengths near the so-called "surface plasmon resonance" condition, the optical reflectivity of the gold changes very sensitively with the presence of biomolecules on the gold suface or in a thin coating on the gold. The extent of binding between the solution-phase interactant and the immobilized antibody is easily observed and quantified by monitoring this reflectivity change.

High pressure liquid chromatography (HPLC) may be employed to detect xanthurenic acid-8-O-b-D-glucoside in urine. For example, urine sample solid phase extraction on a $C_{18}$ cartridge and subsequent passage over a cation-exchange resin column may be employed. Sample detection may be via UV, fluorescence, or light scattering techniques. (see, for example, Marsilio et al., Clinical Chemistry. 1998; 44:1685-1691.) Capillary electrophoresis (CE), or capillary electrophoresis-mass spectrometry (CE-MS) with optional pretreatment of urine sample by solid phase extraction may also be employed to quantitate xanthurenic acid-8-O-β-D-glucoside in biological samples. (He et al., J Chromatogr B Biomed Sci Appl. 1999 Apr. 30; 727(1-2):43-52; Theodoridis et al., J Chromatogram B Biomed Sci Appl. 2000 Aug. 4; 745(1):49-82.)

The invention will now be described in greater detail by reference to the following non-limiting examples.

EXAMPLES

Example 1

Synthesis of Xanthurenic acid 8-O-β-D-glucoside

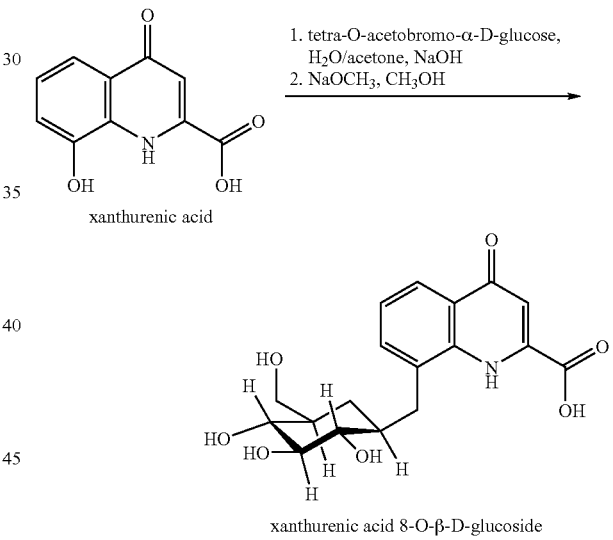

Step 1: Synthesis of xanthurenic acid 2,3,4,6-tetra-O-acetyl 8-O-β-D-glucoside. (See, for example, Real, et al., J. Biol. Chem., 1990, 265(13), 7407-7412)

Xanthurenic acid was obtained commercially from Aldrich, Milwaukee, Wis. Xanthurenic acid (930 mg, 4.53 mmol) in aqueous 1M NaOH (10 mL) was cooled to 10° C. 2,3,4,6-tetra-O-acetyl8-α-D-glucopyranosylbromide (2.03 g, 4.94 mmol) in acetone (16 mL) was added dropwise over 10 minutes. The solution was allowed to warm to room temperature over 4 hours. Additional aqueous 1M NaOH (3 mL) was added slowly over 30 minutes and solution stirred 30 minutes. The mixture was extracted with water and diethyl ether. The aqueous portion was acidified to pH 3.5 and further extracted with 1:1 tetrahydrofuran/ethylacetate. The combined organic layers were washed with saturated aqueous NaCl and dried over magnesium sulfate. Following filtration, the crude xanthurenic acid tetra-O-acetyl 8-β-D-glucoside intermediate was concentrated in vacuo to give approximately 1 gram of a crude residue. The residue was triturated with 4:1 dimethylsulfoxide/water (28 mL), filtered and dried to return 215 mg of xanthurenic acid tetra-O-acetyl 8-β-D-glucoside as an off-white solid intermediate. The mother liquor was further purified by high-pressure liquid chromatography (HPLC) to recover an additional 60 mg of intermediate (C18, water/acetonitrile with 0.2% trifluoroacetic acid; step elution) for a combined 11.5% yield. $^1$H NMR (300 MHz, DMSO-$d_6$) δ 1.97 (s, 3H), 1.99 (s, 3H), 2.00 (s, 3H), 2.06 (s, 3H), 4.05-4.30 (m, 3H), 5.07 (d, J=9.6 Hz, 1H), 5.23 (dd, J=9.6, 7.8 Hz, 1H), 5.44 (t, J=9.60 Hz, 1H), 5.67 (d, J=7.8 Hz, 1H), 6.65 (s, 1H), 7.37 (t, J=8.1 Hz, 1H), 7.48 (dd, J=7.5, 1.2 Hz, 1H), 7.81 (dd, J=8.1, 1.2 Hz, 1H), 9.44 (bs, 1H). ESI-MS m/z 536.44 (M+H$^+$).

Step 2: Xanthurenic acid 8-O-β-D-glucoside.

Xanthurenic acid 2,3,4,6-tetra-O-acetyl 8-O-β-D-glucoside from step 1 (190 mg, 0.35 mmol) was added to a solution of 95% sodium methoxide (40 mg, 0.7 mmol) in methanol (5 mL). The mixture was stirred for one hour. The mixture was adjusted to pH 3.5 with aqueous 1M HCl. The slurry was diluted with 20 mL diethyl ether and filtered. The filter cake was washed with 1:1 methanol/diethyl ether and dried in vacuo to give 118 mg of xanthurenic acid 8-O-β-D-glucoside in an 82% yield. FTIR (neat) 3000-3700 (br s), 3365, 2934, 1626, 1602 cm$^{-1}$. $^1$H NMR (300 MHz, DMSO-$d_6$) δ 3.10-3.70 (m, 6H and H$_2$O), 4.87 (d, J=7.5 Hz, 1H), 4.95 (m, 1H), 5.16 (m, 1H), 5.33 (m, 1H), 5.81 (m, 1H), 6.47 (s, 1H), 7.21 (t, J=8.0 Hz, 1H), 8.07 (d, J=7.2 Hz, 1H), 8.24 (dd, J=8.4, 1.0 Hz, 1H), 8.47 (s, <1H, partial exchange), 10.47 (br s, 1H). $^{13}$C-NMR (75.4 MHz, DMSO-$d_6$) δ 60.74, 69.62, 73.49, 76.56, 77.66, 103.73, 107.73, 119.65, 122.72, 126.79, 132.00, 146.24, 147.05, 162.85, 166.88, 178.33. Electrospray ionization mass spectra (ESI-MS) m/z 368.31 (M+H$^+$).

Example 2

Synthesis of Xanthurenic acid 8-O-sulfate

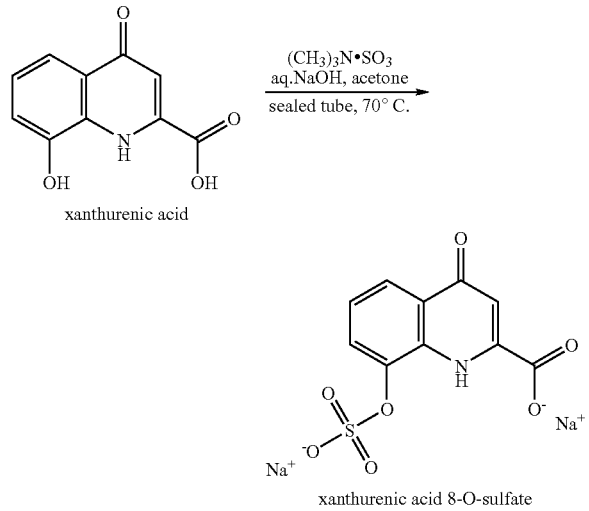

To a solution of xanthurenic acid (300 mg, 1.46 mmol) in 2.9 mL of 1 N NaOH and 2.1 mL of dH$_2$O (deionized water) were added sulfertrioxide trimethylamine (407 mg, 2.92 mmol) and 5 mL of acetone at room temperature. The reactor (20×125 mm tube) was sealed under nitrogen and stirred at 70° C. for 16 hours. The reaction was cooled to room temperature and concentrated to dryness under reduced pressure. The residue was washed with acetone, acetonitrile, dichloromethane, ethyl acetate and then diethyl ether consecutively. The collected solid was placed under vacuum overnight. The solid was dissolved in 3 mL dH$_2$O, loaded to a SEPHADEX SP-C25 column (4×11 cm, 40-125μ) and eluted with dH$_2$O to afford the sodium salt of the title compound (474 mg, 1.44 mmol) in a 98.8% yield as a shiny brown powder with mp>250° C. (dec.). $^1$H NMR (300 MHz, D$_2$O) δ 6.67 (br s, 1H), 7.28 (br dd, J=8.1, 7.8 Hz, 1H), 7.56 (br d, J=7.8 Hz, 1H), 7.79 (br d, J=8.1 Hz, 1H). $^{13}$C NMR (75 MHz, D$_2$O) δ 108.5, 122.1, 124.9 125.6, 126.1, 132.6 140.7, 144.7, 166.3, 181.0. IR (solid, cm$^{-1}$) 2835, 2545, 1687, 1601, 1372, 1372, 1254.

Example 3

Isolation of Xanthurenic Acid 8-O-sulfate and Xanthurenic Acid 8-O-β-D-glucoside Urine samples from human uremic patients were collected over 24-hour periods. The typical collection volume was of 2-3 liters per patient. Individual samples were lyophilized to dryness and reconstituted with 100 mL of deionized water. The reconstituted samples (25 mL load volume) were size-fractionated using gel filtration SEPHADEX G-25 column chomatography with elution by 10 mM ammonium acetate, pH 6.8 at 10° C. and monitored by UV at 285 nm and conductivity. Later eluting (post-salt peak) 10 mL fractions with UV activity and osmolality <100 mOsm were screened for biological activity with the frog skin assay of Bricker et al. (Kidney International Vol 44 (1993) November; 44 (5): 937-47). Fractions with activity (10 mL each) were concentrated by lyophilization and reconstituted with 1 mL dionized water.

Reconstituted Sephadex G-25 fractions with biological activity were further fractionated with high performance liquid chromatography (HPLC; 1 mL load volume) over an octadecylsilyl (Phenomenex SphereClone ODS2, 35° C.) semi-preparative HPLC column at 4 mL/minute with a 0.1 M pyridium acetate: methanol gradient; 0-40% methanol/11 minutes with collection of 2 mL fractions. Elution was monitored by fluorescence (excitation 332 nm, emission at 430 nm) and UV (338 nm). Fractions with a retention time (RT) of 12.4 minutes were pooled from multiple runs and concentrated approximately 10-fold. The fractions were re-applied to the HPLC system above with a 1 mL injection volume run in isocratic mode with 92% 0.1 M/8% methanol at 4 mL/minute. Fluorescence was monitored with excitation 332 nm, emission 430 nm. UV was monitored at 338 nm. These maxima are for xanthurenic acid 8-O-β-D-glucoside. Eluate between 10-13 minutes was collected in 12 second (0.8 mL) fractions. Fractions eluting between 11.2-11.6 minutes RT contained xanthurenic acid 8-O-β-D-glucoside; fractions eluting between 12.0-12.5 minutes contained xanthurenic acid 8-O-sulfate. Fractions containing either the xanthurenic acid 8-O-β-D-glucoside or the xanthurenic acid 8-O-sulfate were separately pooled and concentrated on a Savant Speed-Vac Plus (SC210A) with medium heat. The pools were resubjected to isocratic HPLC on an analytical scale using a reverse phase C-18 HPLC column: Phenomenex P/NO 00G-4375-E0, SYNERGI 4u Hydro-RP 80A 250×4.6 mm, 4 micron. The HPLC purification was run in isocratic mode at 1 mL/minute with 8% methanol and 0.1% 0.1M pyridium acetate at 35° C. Elution was monitored by UV absorbance at 338 nm and fluorescence detection with excitation 332 nm, emission 430 nm. Fractions containing xanthurenic acid 8-O-β-D-glucoside had RT=10.2-10.6 minutes. Fractions from separate xanthurenic acid 8-O-sulfate runs had RT=11-11.5 minutes. Fractions were pooled and concentrated on a Speed-Vac, with occasional addition of pyridine to increase pH. The purified xanthurenic acid 8-O-β-D-glucoside was reapplied to the same analytical column and eluted with 20% methanol in water to eliminate pyridium acetate. Xanthurenic acid 8-O-β-D-glucoside formed crystals upon concentration by this technique. For isolated xanthurenic acid 8-O-β-D-glucoside ($C_{16}H_{17}NO_9$): ESI-MS (m/z) 367.09, 368.094 (M+H) and 229 (M-glucose+$Na^+$); $^1$H-NMR (500 MHz, $D_2O$) δ 3.58 (dd, J=9, 9.5 Hz, 1H), 3.65 (dd, J=9, 9.5 Hz, 1H), 3.67 (m, 1H), 3.80 (dd, 1H), 3.81(dd, J=8, 9.5 Hz), 3.95 (dd, 1H), 5.24 (d, J=8 Hz, 1H), 6.93 (s, 1H), 7.47 (t, J=8 Hz, 1H), 7.59 (dd, J=8, 2 Hz, 1H), 7.90 (dd, J=8, 2 Hz) ppm; $^{13}$C-NMR (126 MHz, $D_2O/CD_3OD$) δ 60.8, 69.7, 72.9, 75.7, 76.7, 101.2, 108.1, 117.9, 118.2, 124.5, 125.2, 130.6, 143.9, 145.5, 165.9, 180.3 ppm. For isolated xanthurenic acid 8-O-sulfate ($C_{10}H_7NO_7S$): ESI-MS (m/z) 284.994, 285.998 (M+$H^+$).

Example 4

Figure 3:
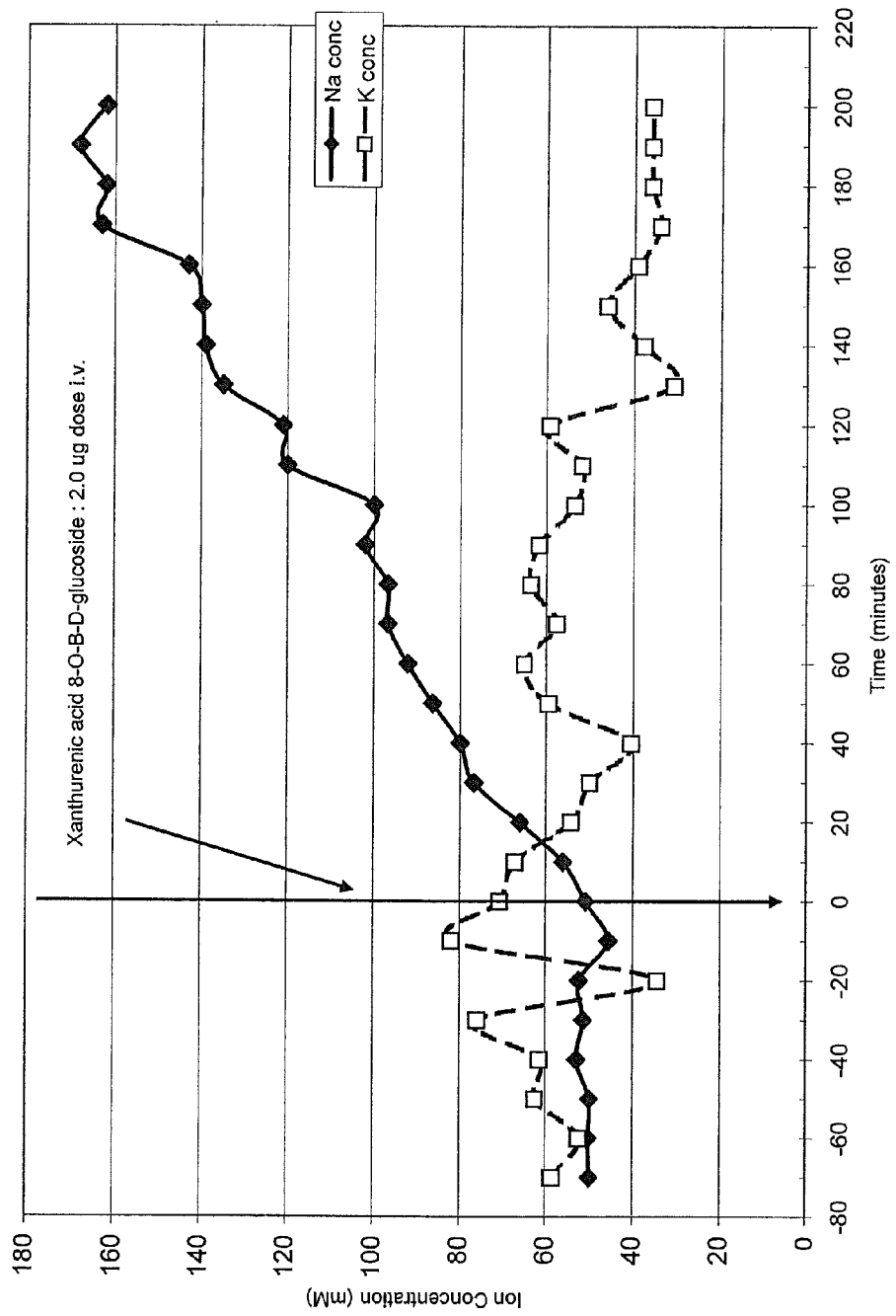
FIG. 3 shows Na$^+$ and K$^+$ concentration in urine following i.v. administration (2 µg dose) of synthetic xanthurenic acid 8-O-β-D-glucoside in a normal Sprague Dawley rat.
Figure 4:
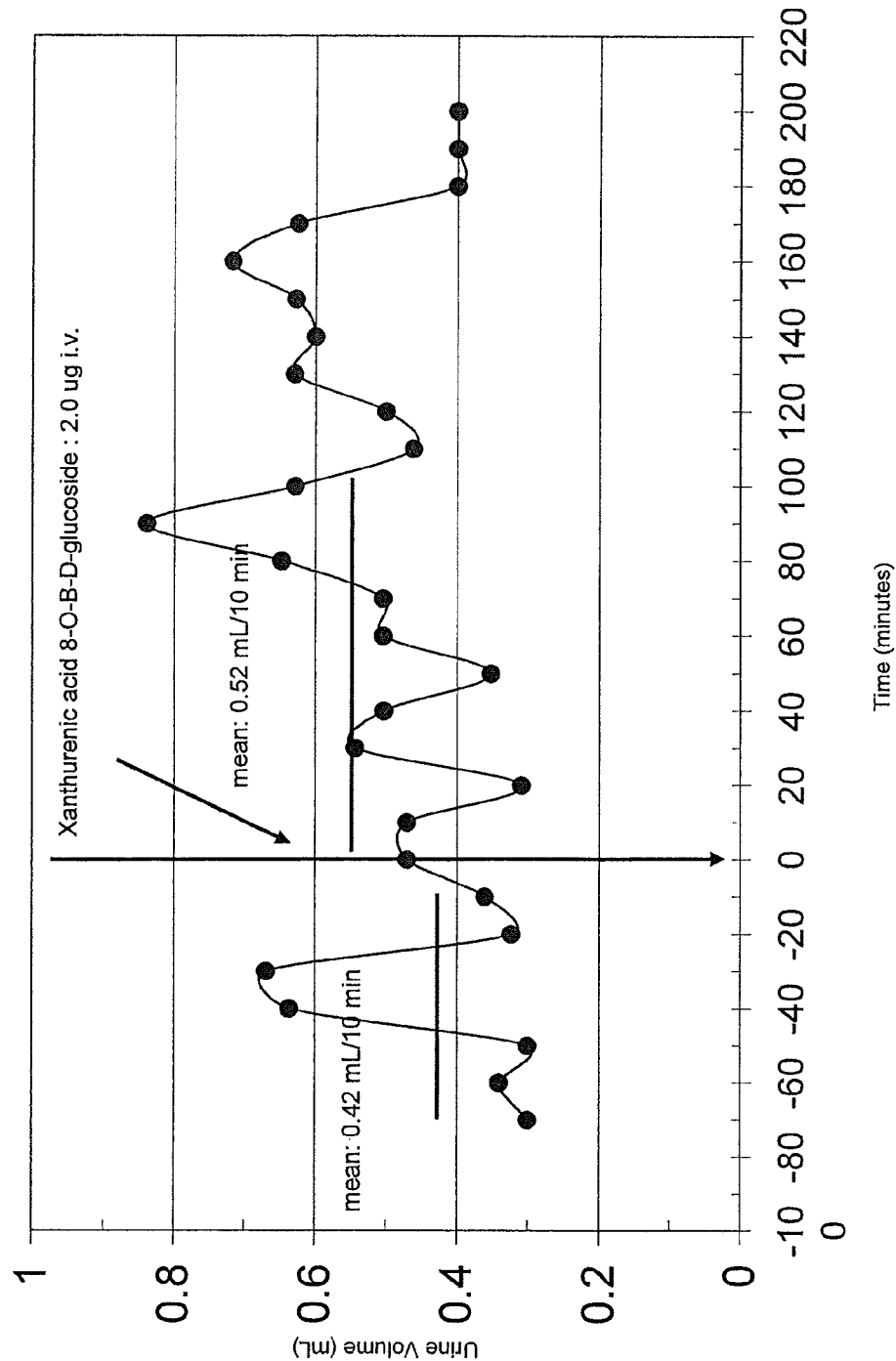
FIG. 4 shows urine volume following i.v. administration (2 µg dose) of synthetic xanthurenic acid 8-O-β-D-glucoside in a normal Sprague Dawley rat.
Figure 5:
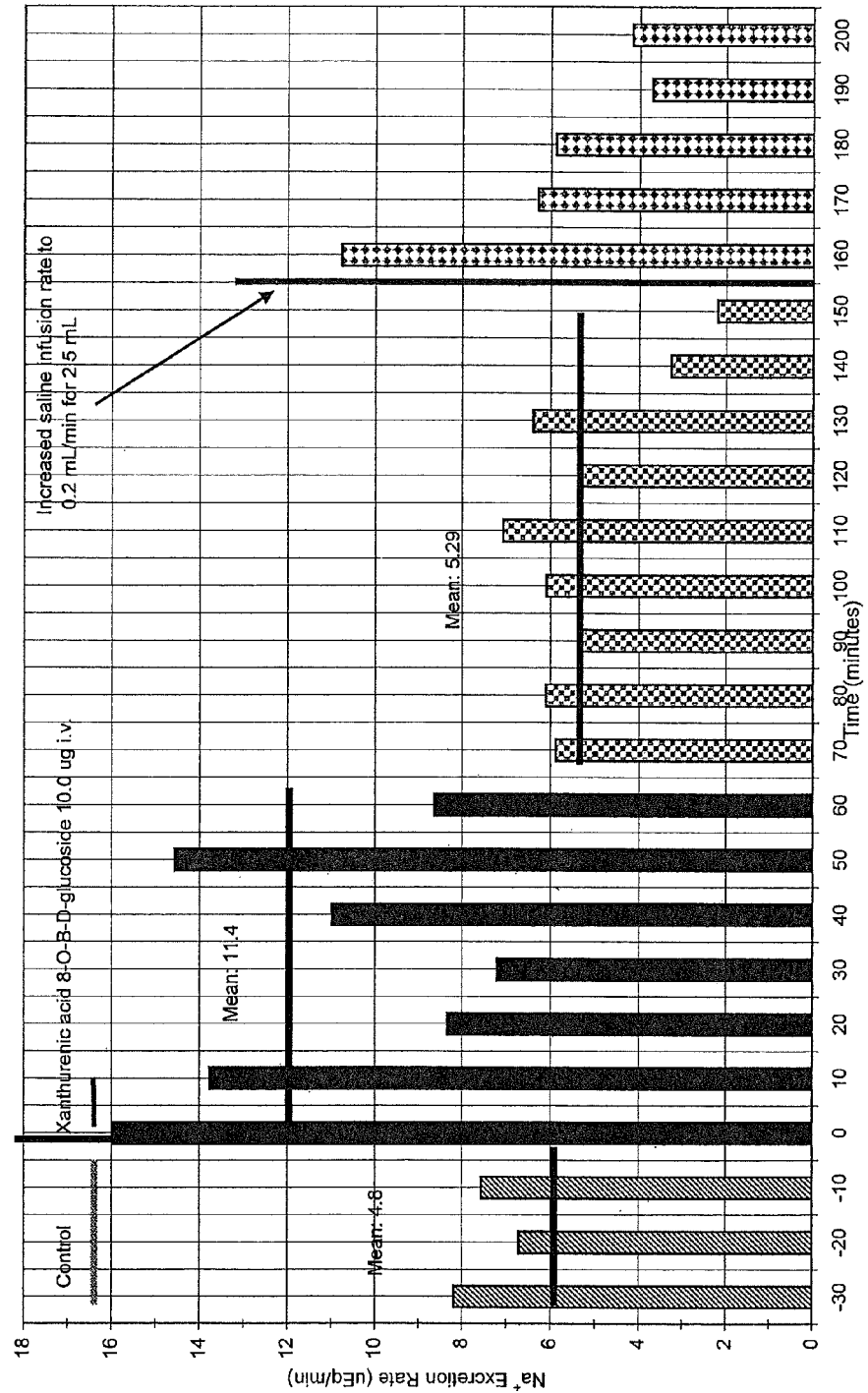
FIG. 5 shows Na$^+$ excretion in response to i.v. administration (10 µg dose) of synthetic xanthurenic acid 8-O-β-D-glucoside in a normal Sprague Dawley rat.
Figure 6:
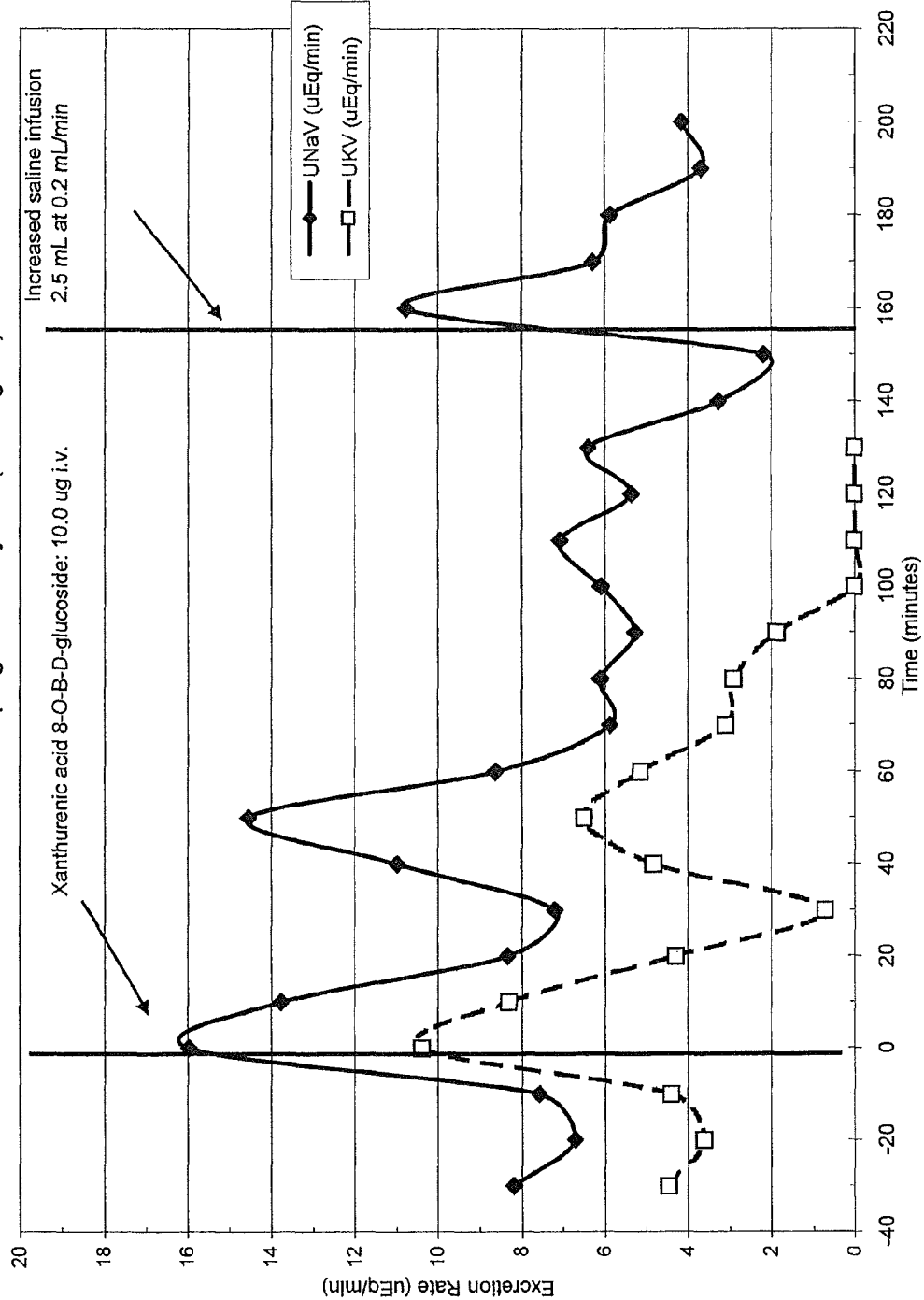
FIG. 6 shows Na$^+$ and K$^+$ urine excretion in response to i.v. administration (10 µg dose) of synthetic xanthurenic acid 8-O-β-D-glucoside in a normal Sprague Dawley rat.

Natriuretic Response to Synthetic Xanthurenic Acid 8-O-β-D-glucoside (2 µg i.v.) in a Normal Sprague Dawley Rat A female Sprague Dawley rat (250 g) was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the duration of the assay. The same i.v. catheter was used to inject the test compound. Synthetic xanthurenic acid 8-O-β-D-glucoside, 2 µg, was injected at the time indicated in a 1-mL volume in saline over the course of 10 minutes. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 1-4. Synthetic xanthurenic acid 8-O-β-D-glucoside at 2 ug i.v. caused a sustained natriuretic response in a normal rat. $Na^+$ excretion was due more to increased $Na^+$ urine concentration than increased urine volume as shown in FIGS. 3 and 4. Given an extracellular volume of 50 mL in a 250-g rat, the concentration of the test compound was $10^{-6}$ M, a possible minimum dose. In a similar experiment; synthetic, underivatized xanthurenic acid at 2 ug i.v. did not increase $Na^+$ excretion. However, subsequent administration of synthetic xanthurenic acid 8-O-β-D-glucoside did cause natriuresis.

Example 5

Figure 7:
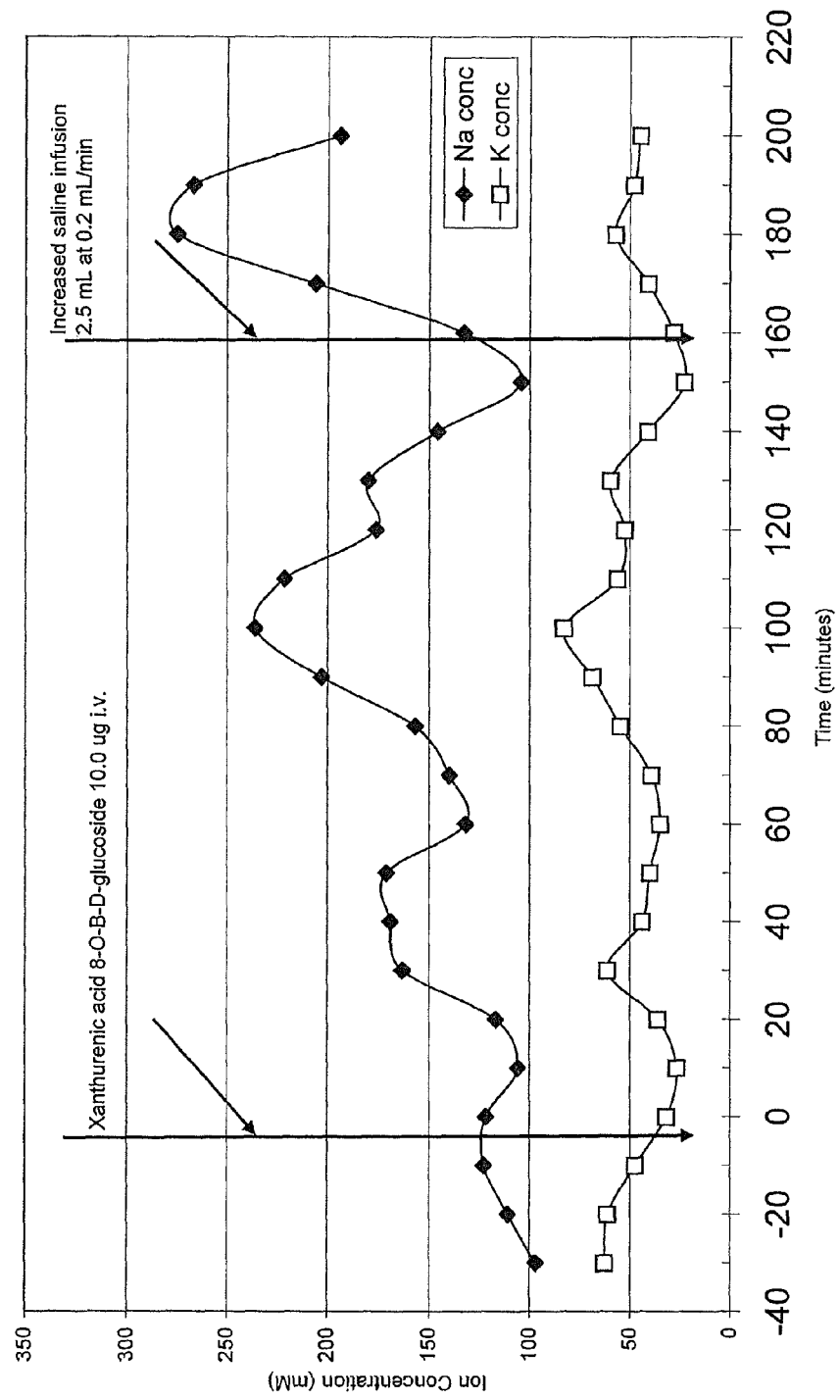
FIG. 7 shows Na$^+$ and K$^+$ concentration in urine in response to i.v. administration (10 µg dose) of synthetic xanthurenic acid 8-O-β-D-glucoside in a normal Sprague Dawley rat.
Figure 8:
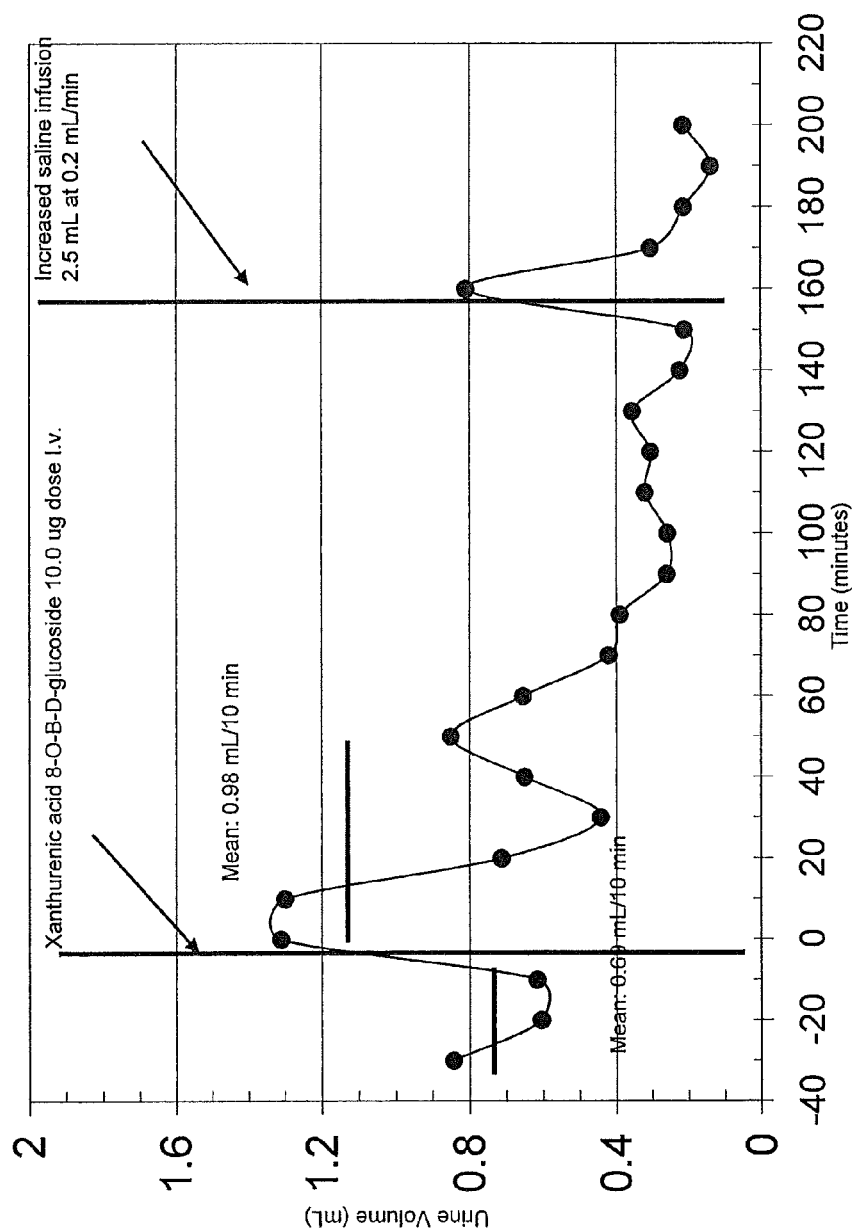
FIG. 8 shows urine volume following i.v. administration (10 µg dose) of synthetic xanthurenic acid 8-O-β-D-glucoside in a normal Sprague Dawley rat.
Figure 9:
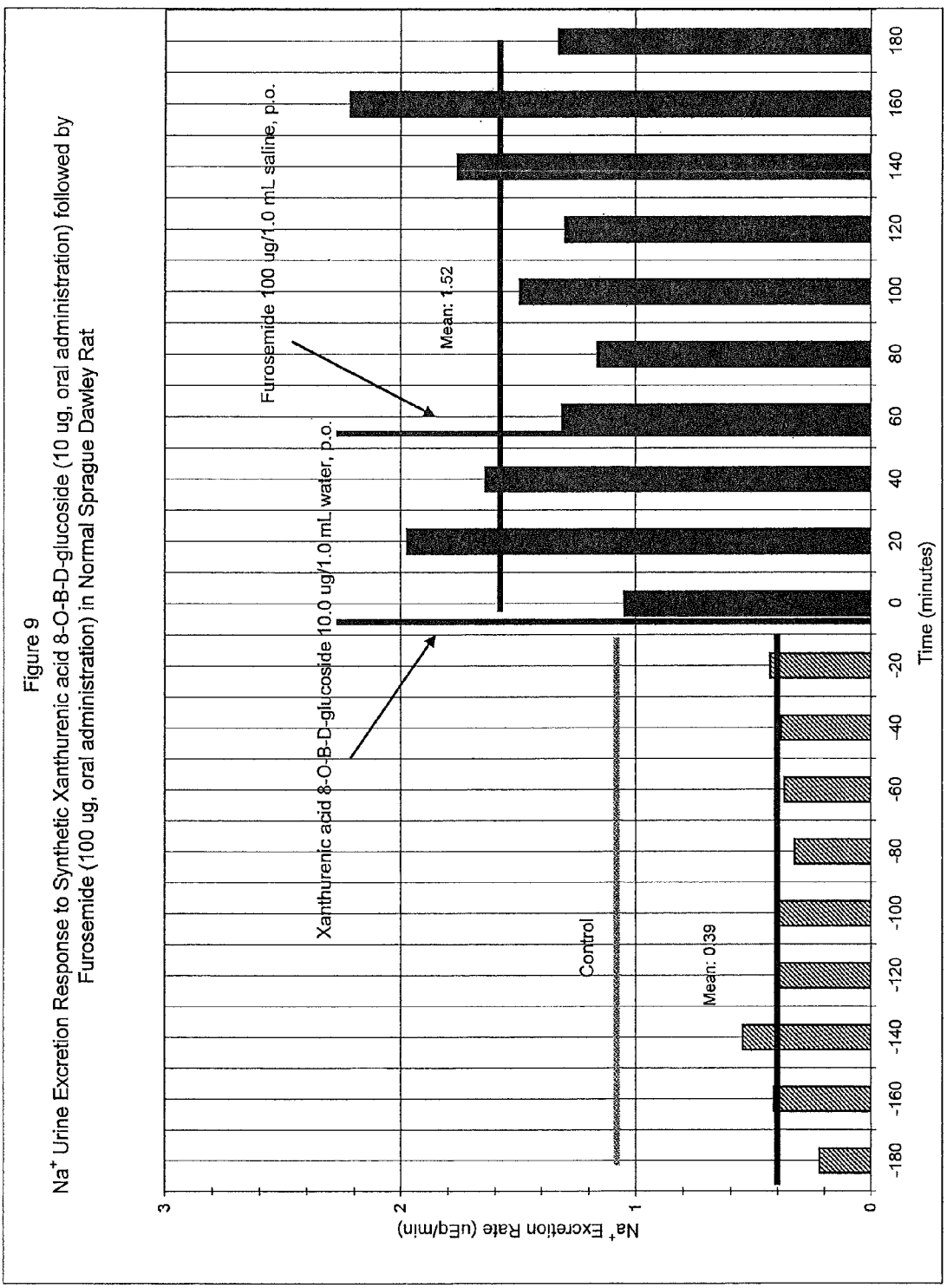
FIG. 9 shows Na$^+$ urine excretion in response to synthetic xanthurenic acid 8-O-β-D-glucoside (10 µg) followed by furosemide (100 µg) in a normal Sprague Dawley Rat, oral (p.o.) administration.
Figure 10:
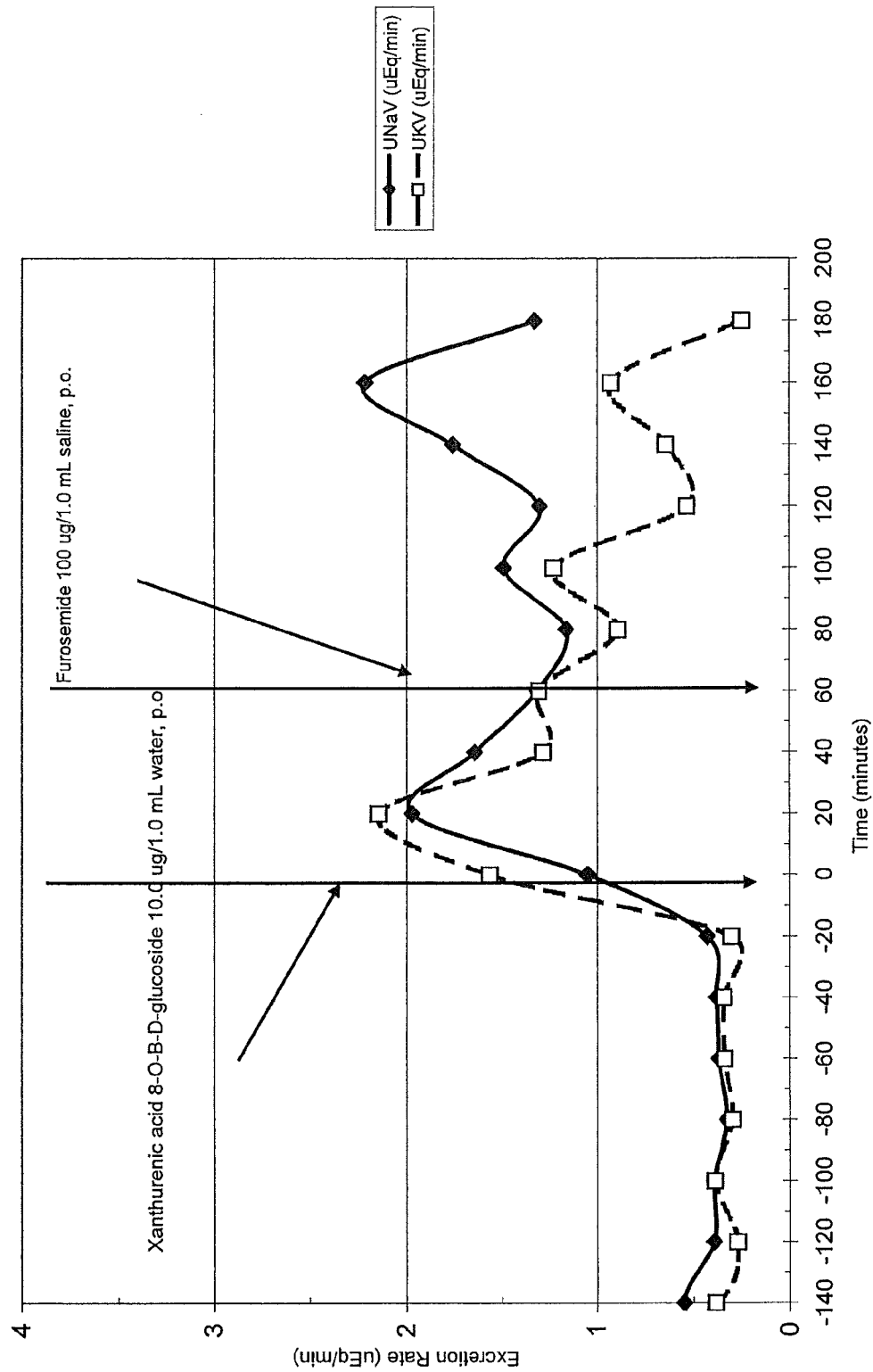
FIG. 10 shows Na$^+$ and K$^+$ urine excretion in response to synthetic xanthurenic acid 8-O-β-D-glucoside (10 µg) followed by furosemide (100 µg) in a normal Sprague Dawley Rat, oral (p.o.) administration.
Figure 11:
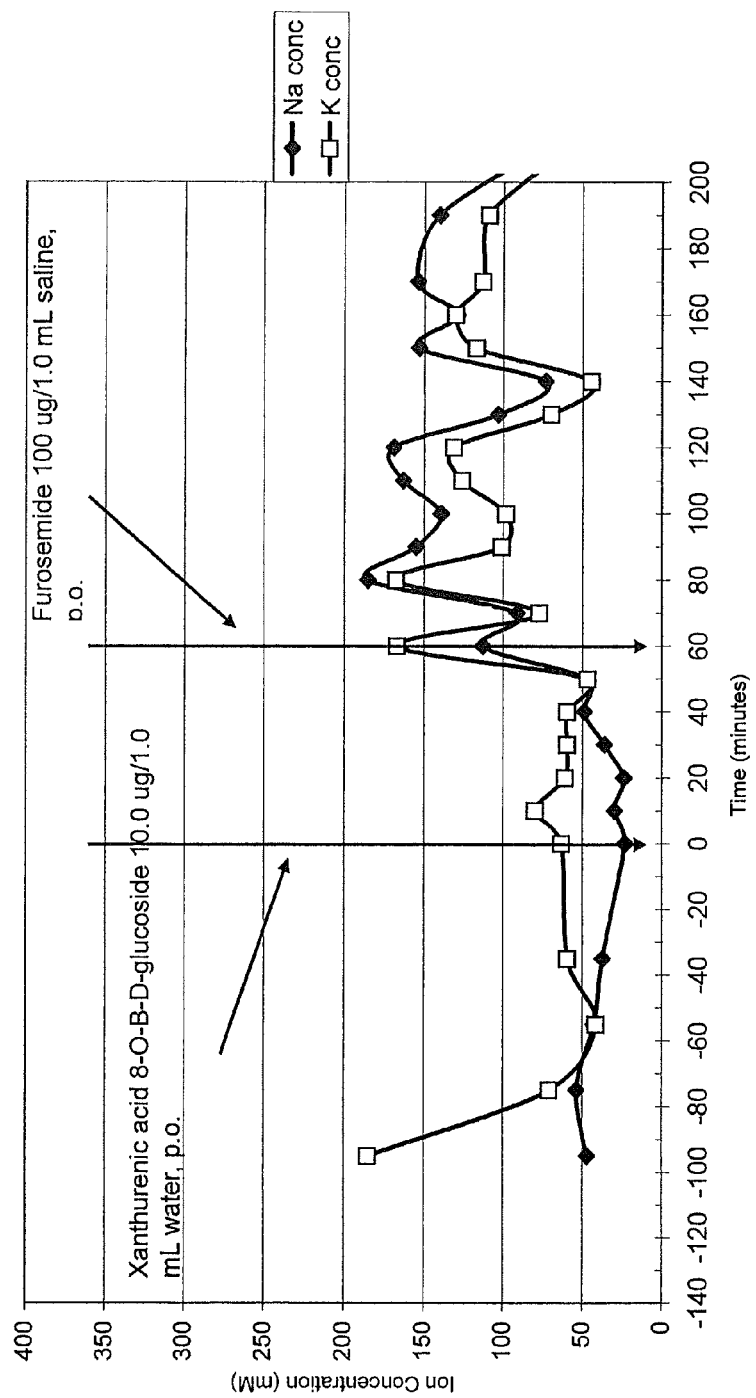
FIG. 11 shows Na$^+$ and K$^+$ concentration in urine in response to synthetic xanthurenic acid 8-O-β-D-glucoside (10 µg) followed by furosemide (100 µg) in a normal Sprague Dawley Rat, oral (p.o.) administration.
Figure 12:
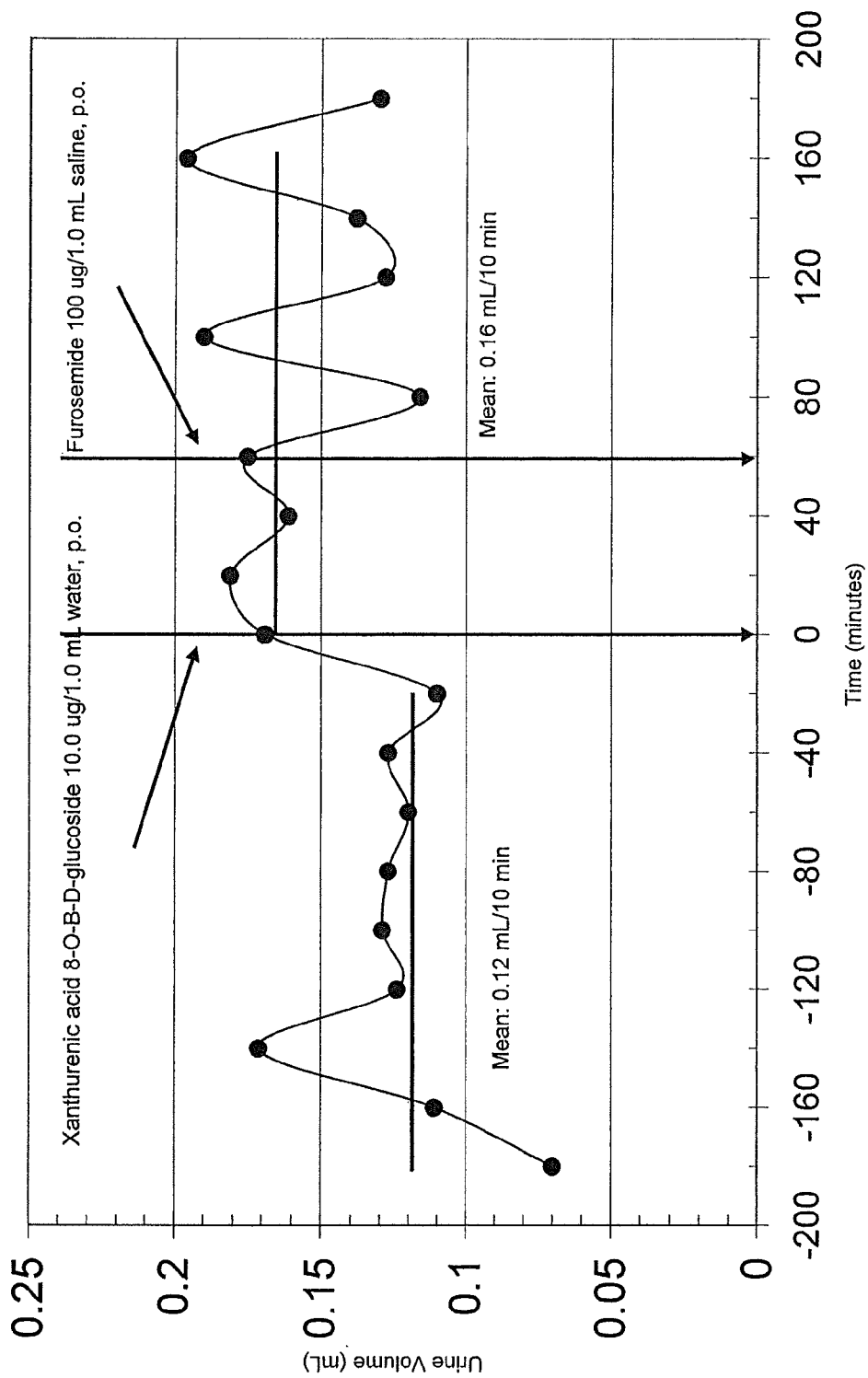
FIG. 12 shows urine volume following administration of synthetic xanthurenic acid 8-O-β-D-glucoside (10 µg) followed by furosemide (100 µg) in a normal Sprague Dawley Rat, oral (p.o.) administration.
Figure 13:
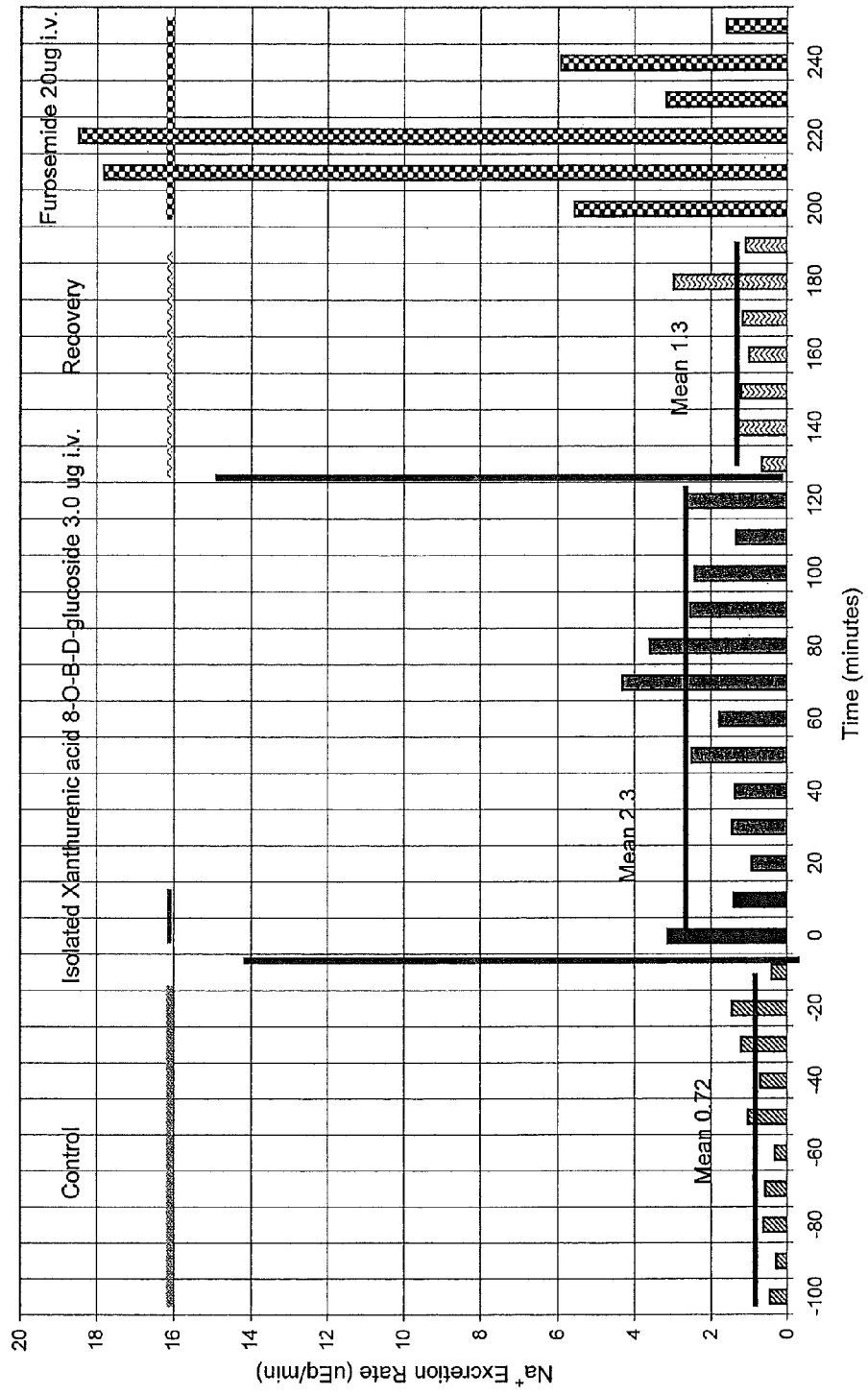
FIG. 13 shows Na$^+$ urine excretion in response to isolated xanthurenic acid 8-O-β-D-glucoside (3 ug) followed by furosemide (20 µg) in a uremic Sprague Dawley rat, i.v. administration.
Figure 14:
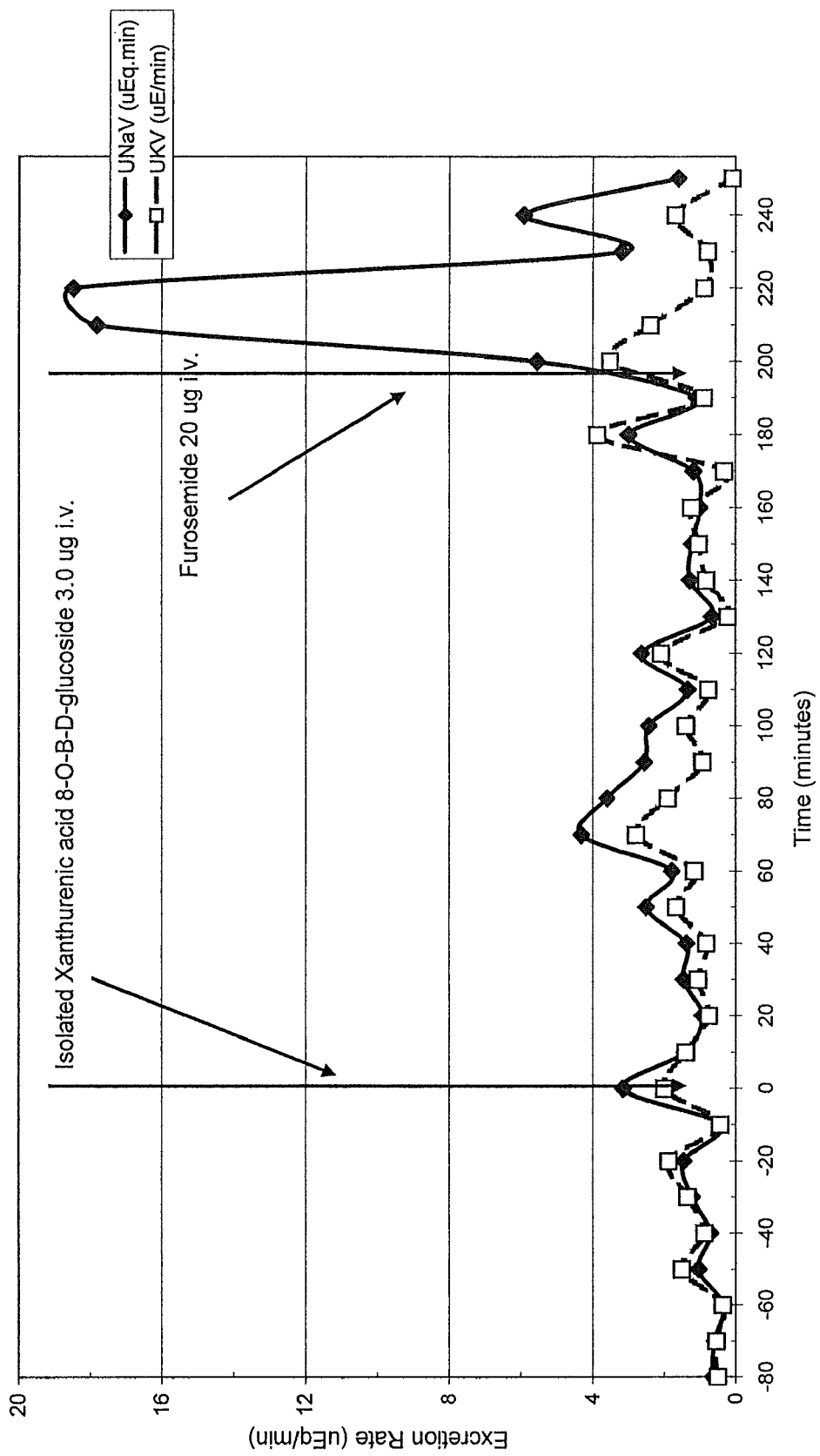
FIG. 14 shows Na$^+$ and K$^+$ urine excretion in response to isolated xanthurenic acid 8-O-β-D-glucoside (3 µg) followed by furosemide (20 µg) in a uremic Sprague Dawley rat, i.v. administration.
Figure 15:
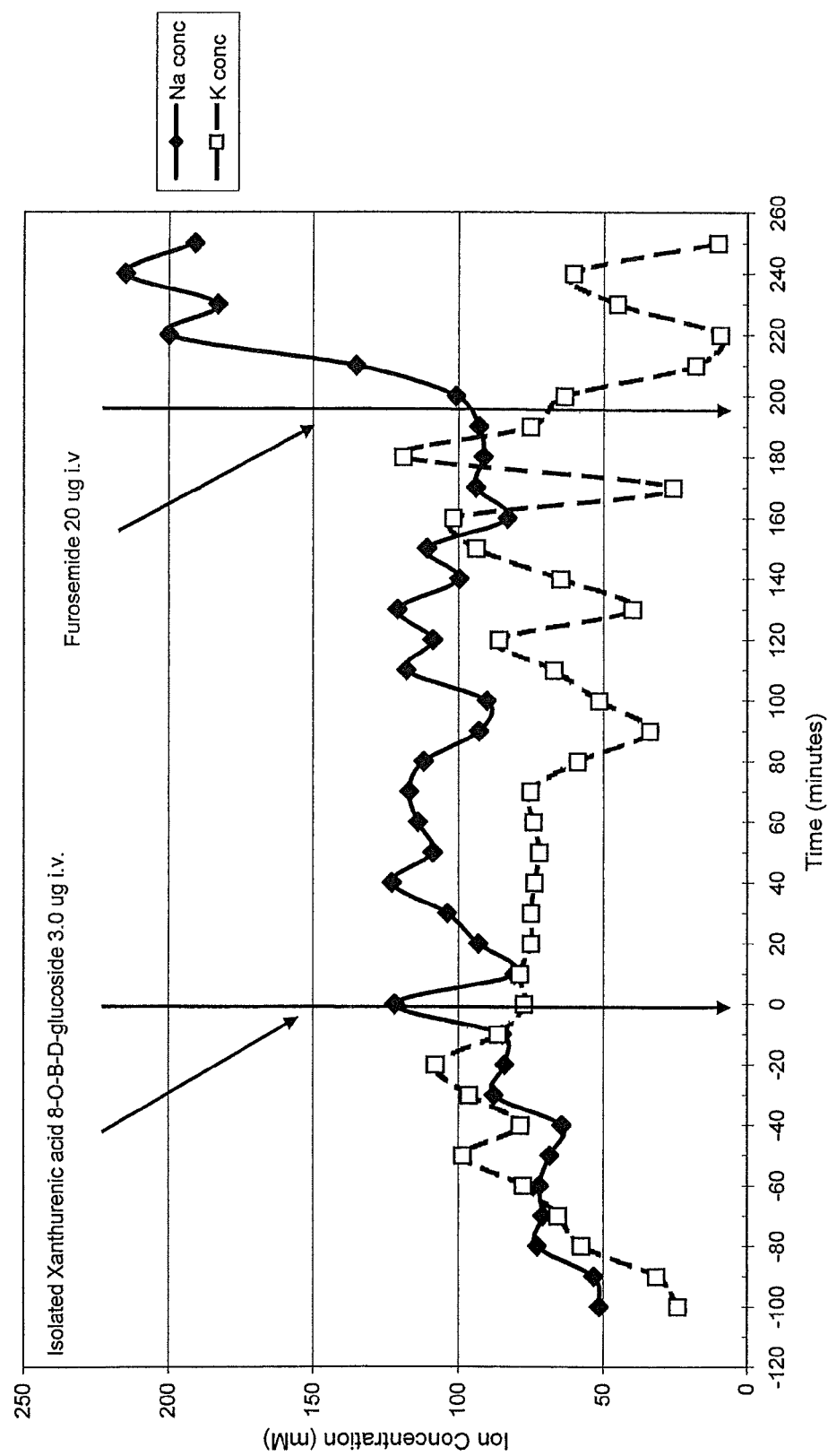
FIG. 15 shows Na$^+$ and K$^+$ urine concentration in urine in response to isolated xanthurenic acid 8-O-β-D-glucoside (3 µg) followed by furosemide (20 µg) in a uremic Sprague Dawley rat, i.v. administration.
Figure 16:
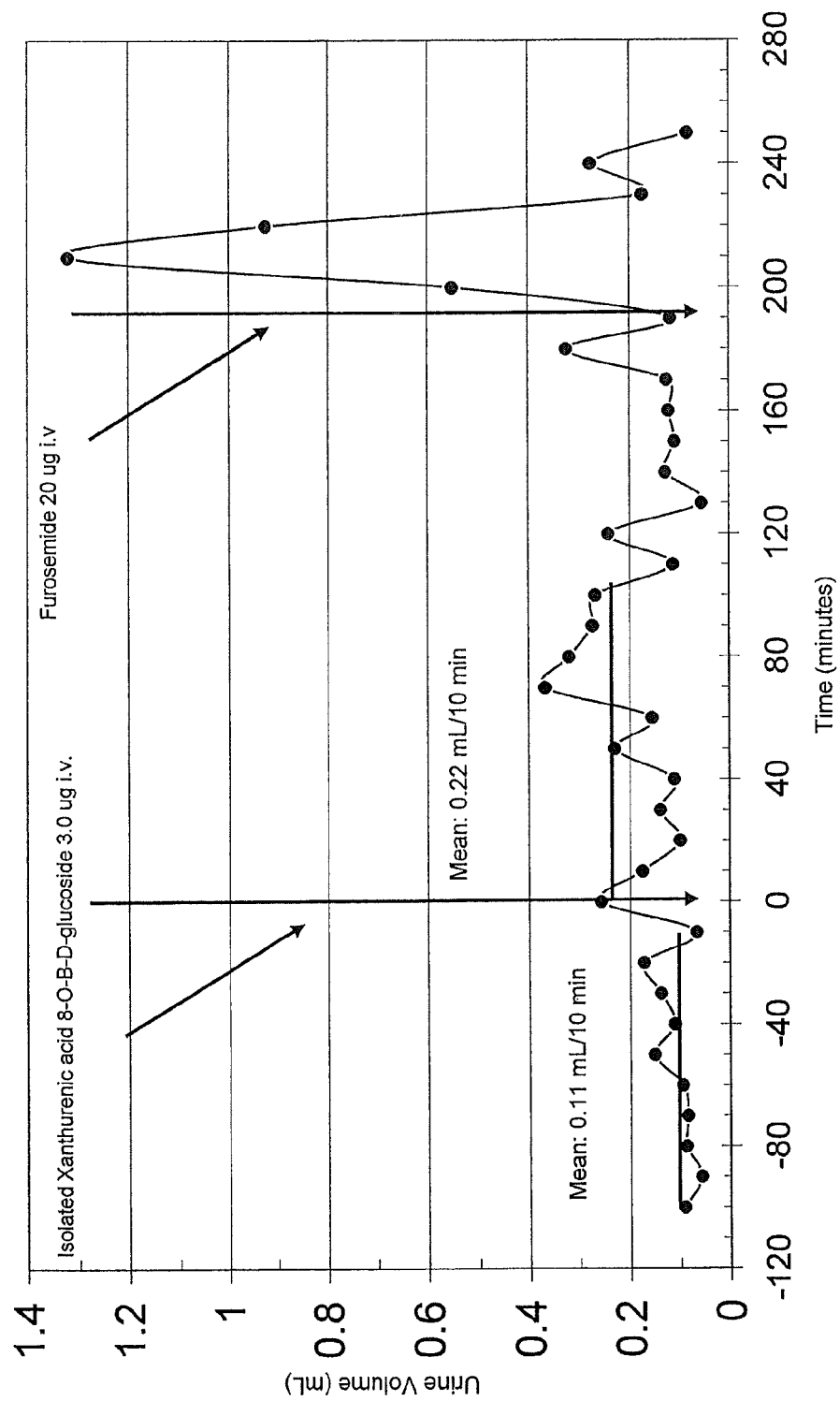
FIG. 16 shows urine volume in response to isolated xanthurenic acid 8-O-β-D-glucoside (3 µg) followed by furosemide (20 µg) in a uremic Sprague Dawley rat, i.v. administration.
Figure 17:
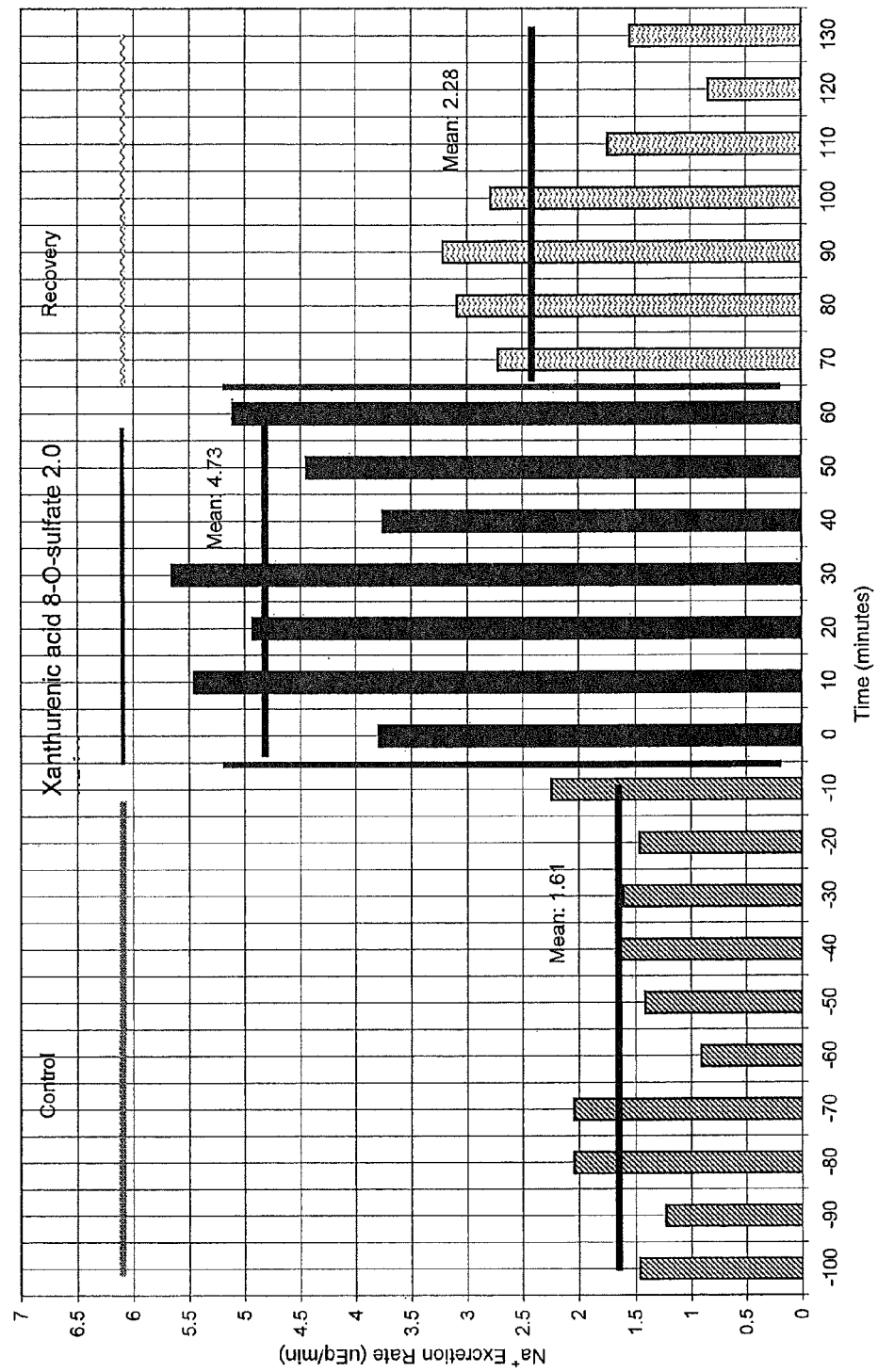
FIG. 17 shows Na$^+$ urine excretion in response to isolated xanthurenic acid 8-O-sulfate (2 µg) in uremic Sprague Dawley rat, i.v. administration.
Figure 18:
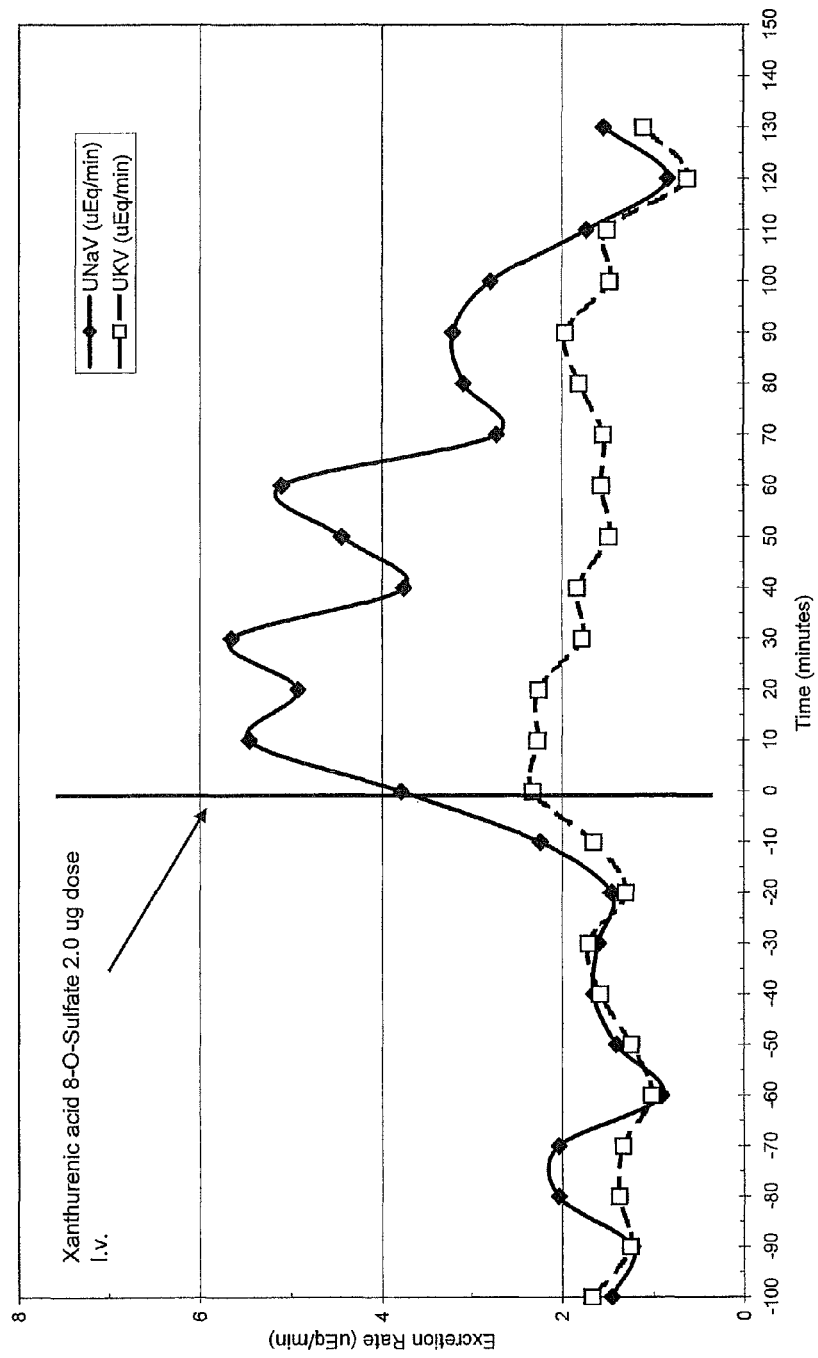
FIG. 18 shows Na$^+$ and K$^+$ urine excretion in response to isolated xanthurenic acid 8-O-sulfate (2 µg) in uremic Sprague Dawley rat, i.v. administration.
Figure 19:
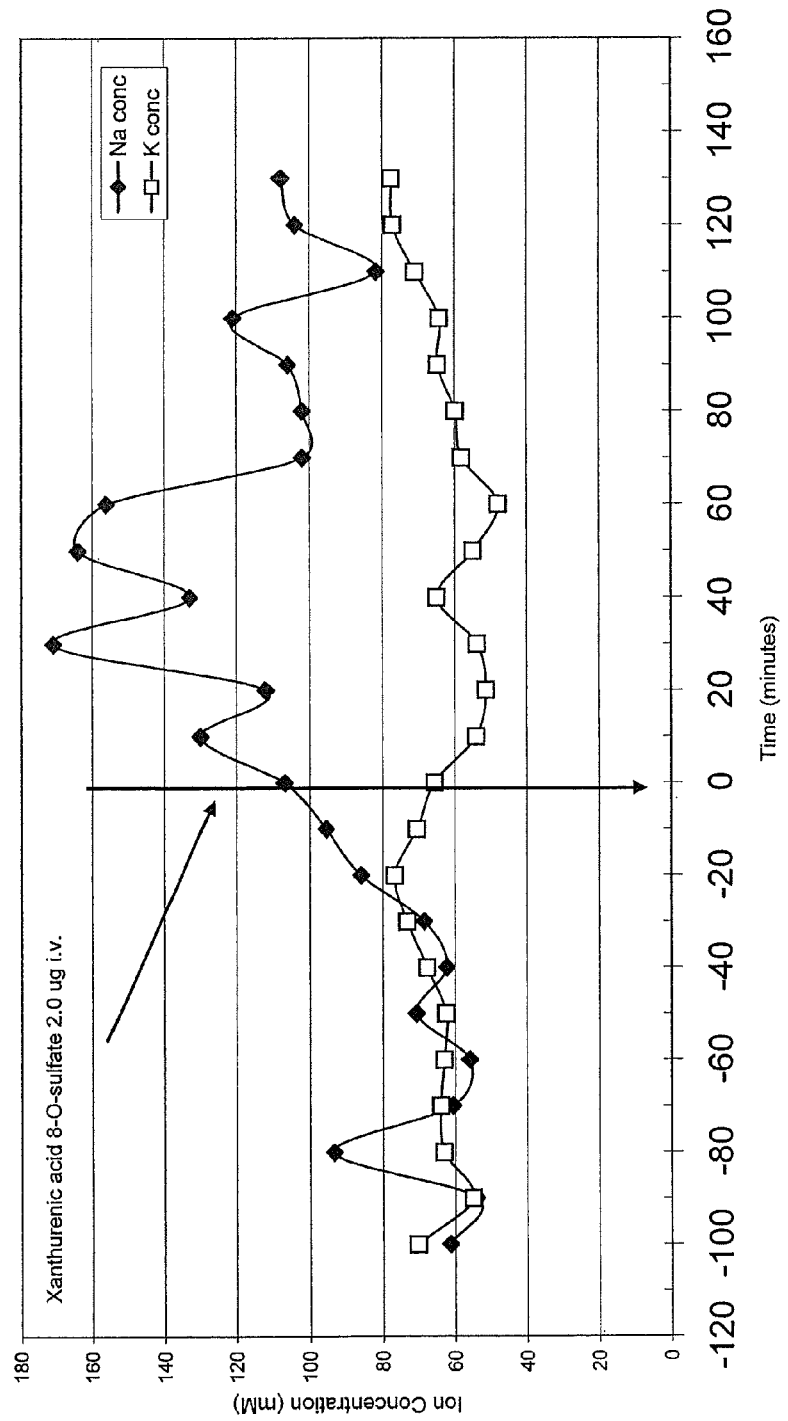
FIG. 19 shows Na$^+$ and K$^+$ urine concentration in urine in response to isolated xanthurenic acid 8-O-sulfate (2 µg) in uremic Sprague Dawley rat, i.v. administration.
Figure 20:
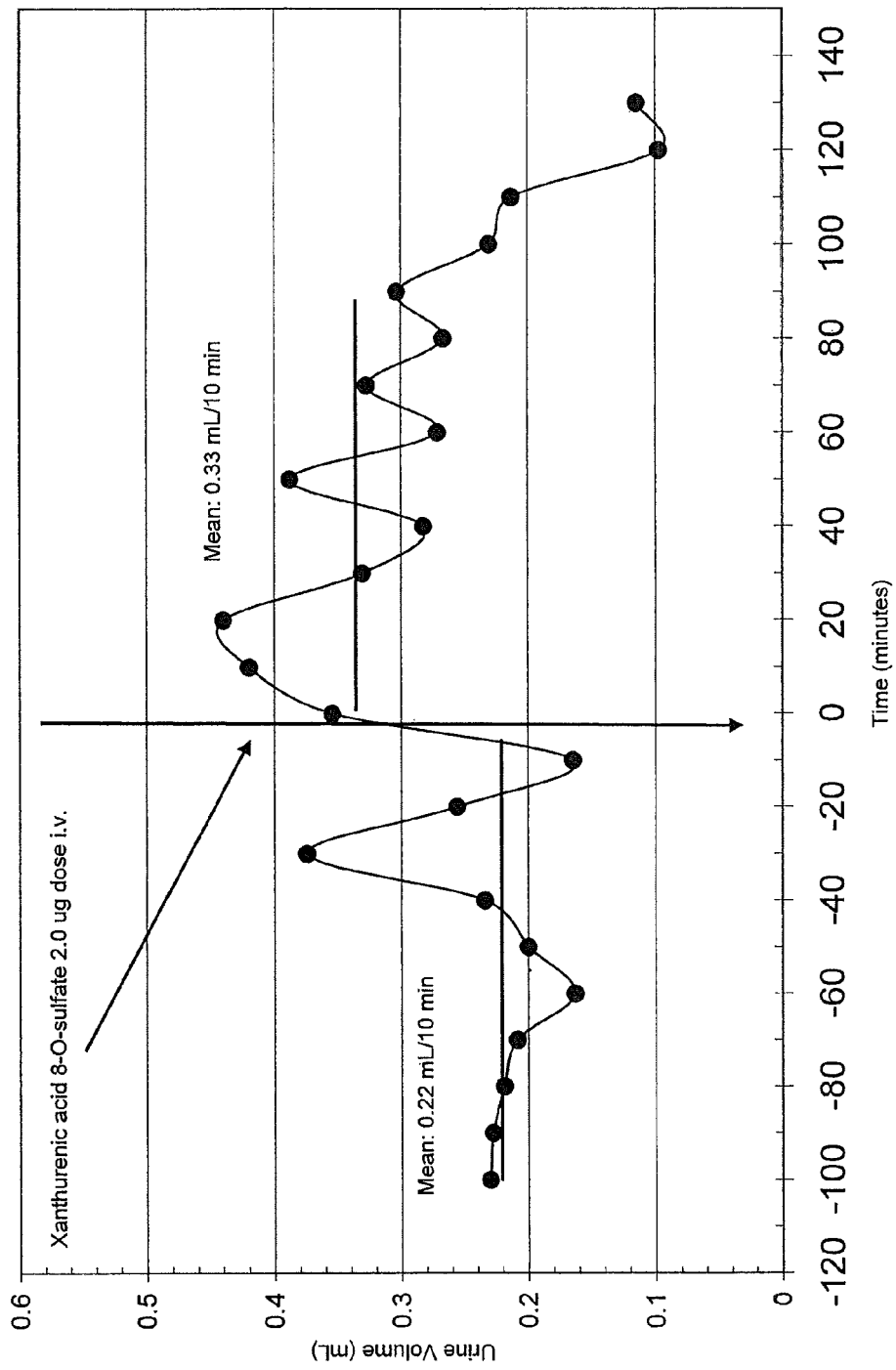
FIG. 20 shows urine volume in response to isolated xanthurenic acid 8-O-sulfate (2 µg) in uremic Sprague Dawley rat, i.v. administration.
Figure 21:
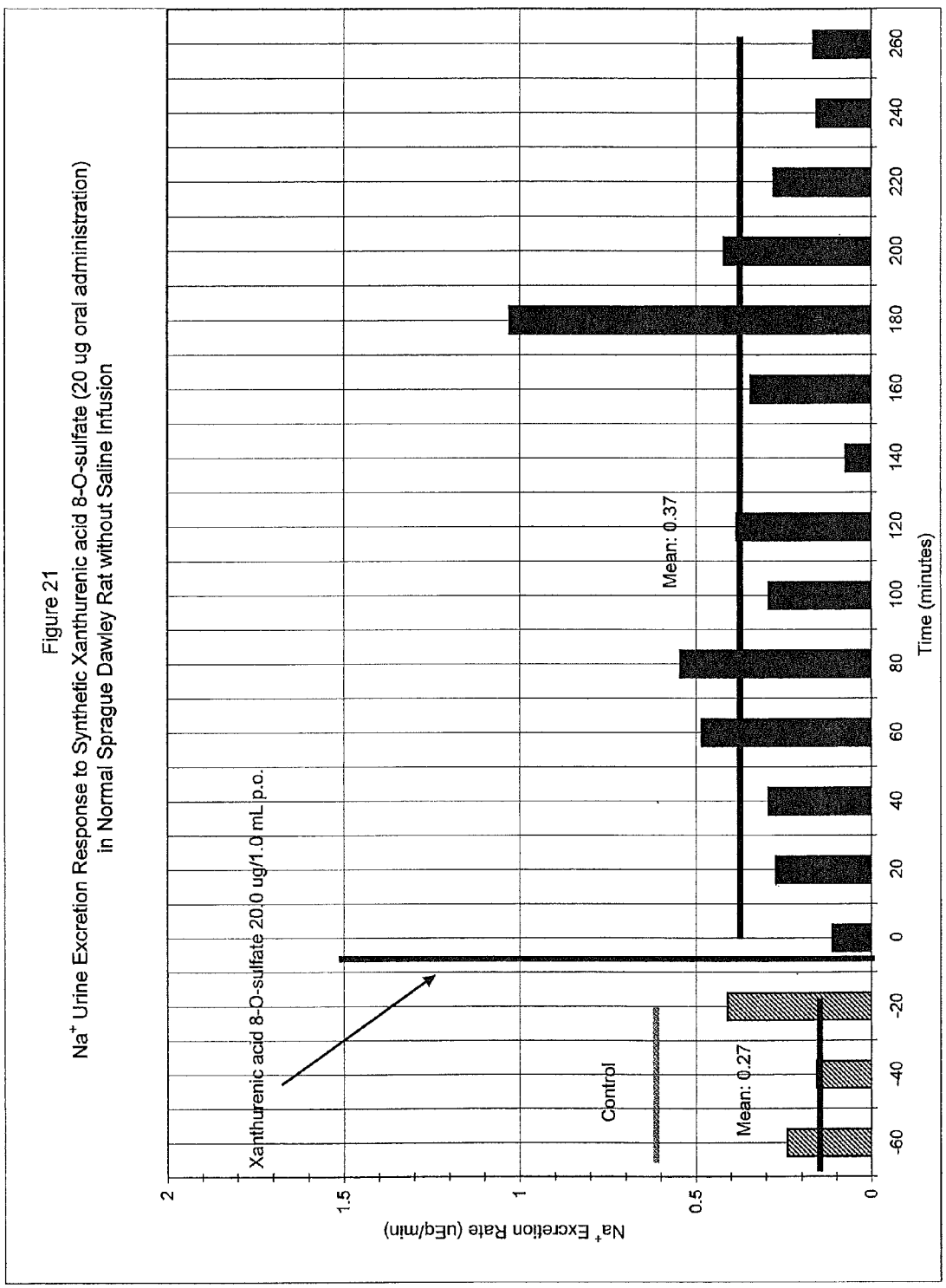
FIG. 21 shows Na$^+$ urine excretion in response to synthetic xanthurenic acid 8-O-sulfate (20.0 ug) in normal Sprague Dawley rat by oral administration.
Figure 22:
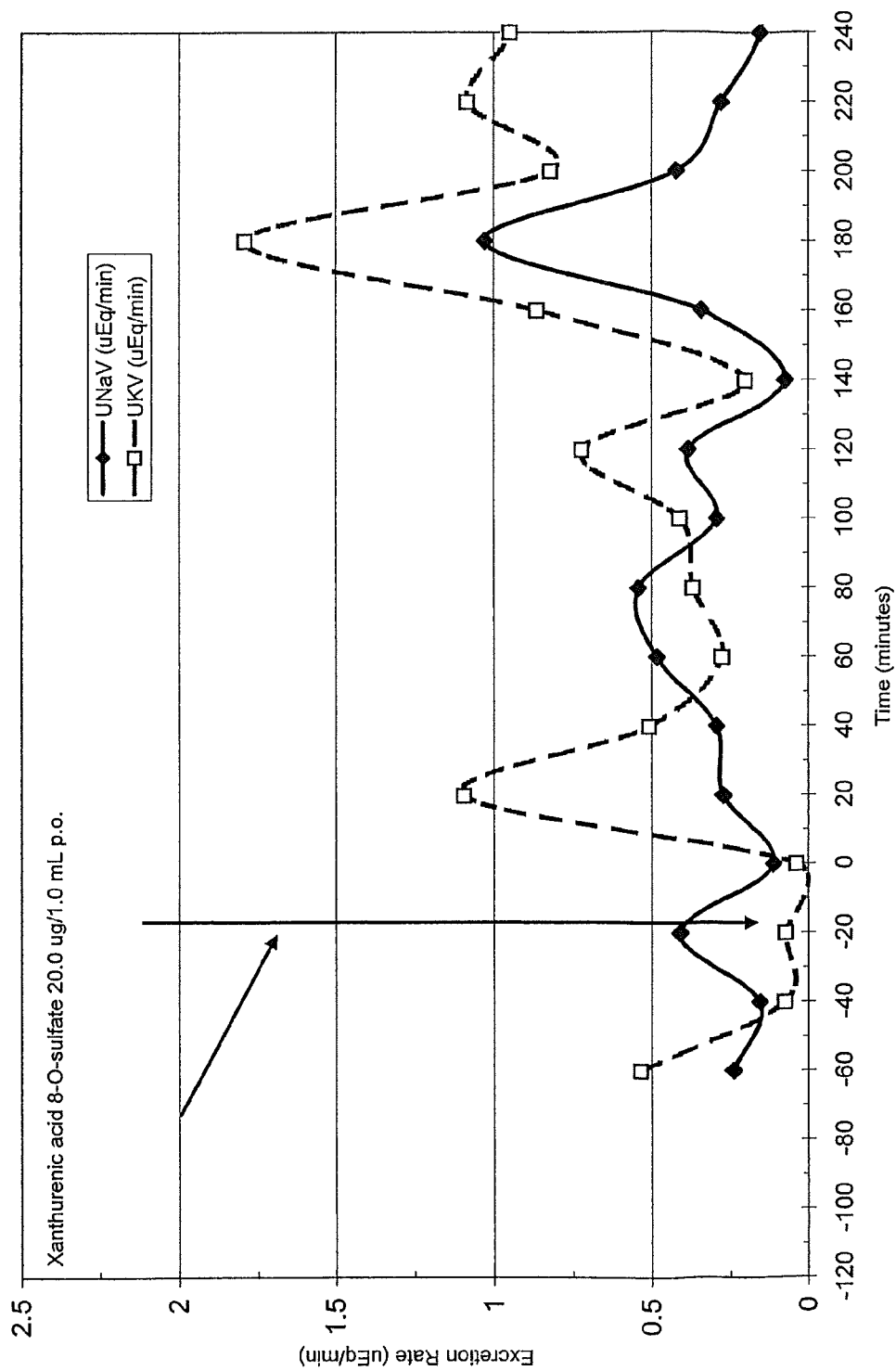
FIG. 22 shows Na$^+$ and K$^+$ urine excretion in response to synthetic xanthurenic acid 8-O-sulfate (20.0 ug) in normal Sprague Dawley rat by oral administration.
Figure 23:
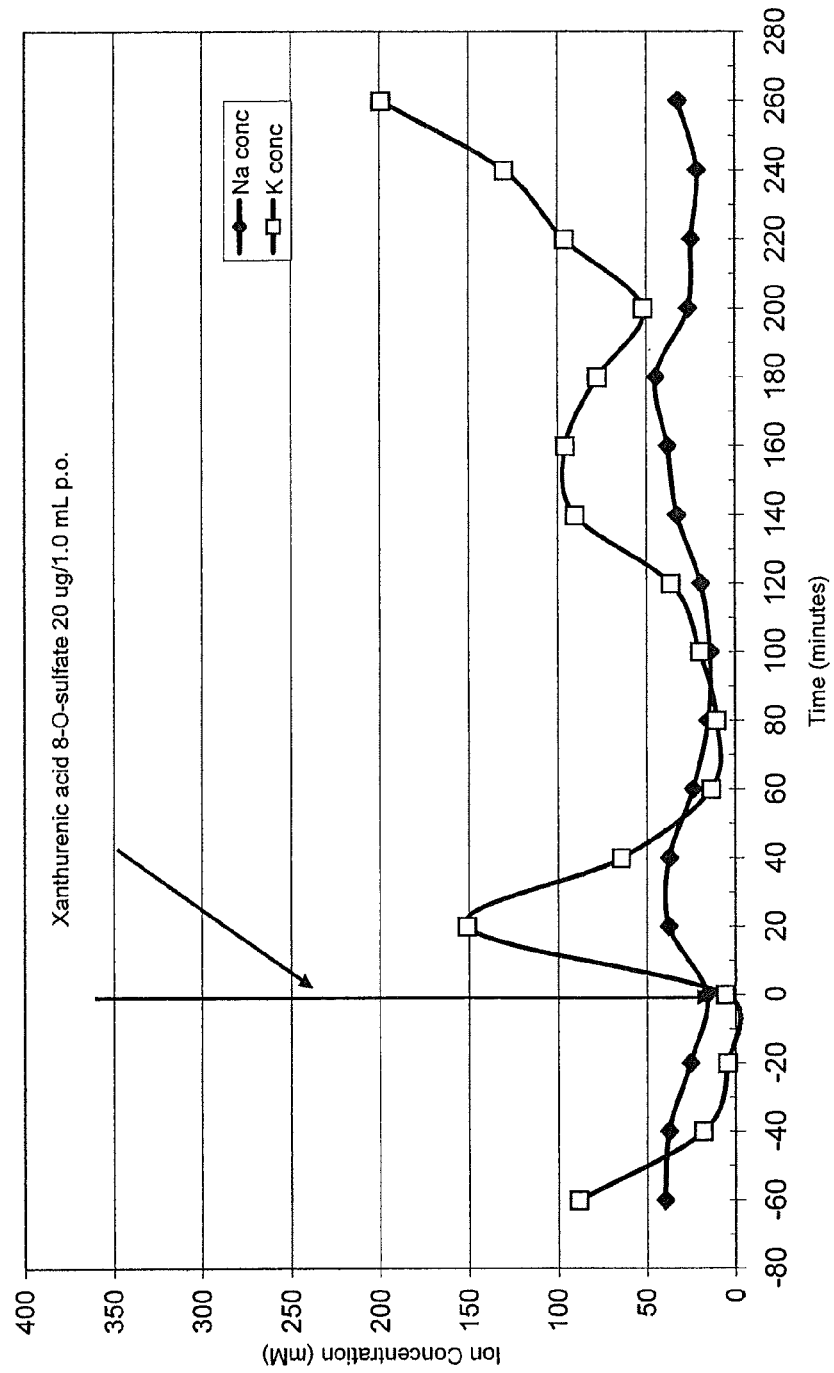
FIG. 23 shows Na$^+$ and K$^+$ concentration in urine in response to synthetic xanthurenic acid 8-O-sulfate (20.0 ug) in normal Sprague Dawley rat by oral administration.
Figure 24:
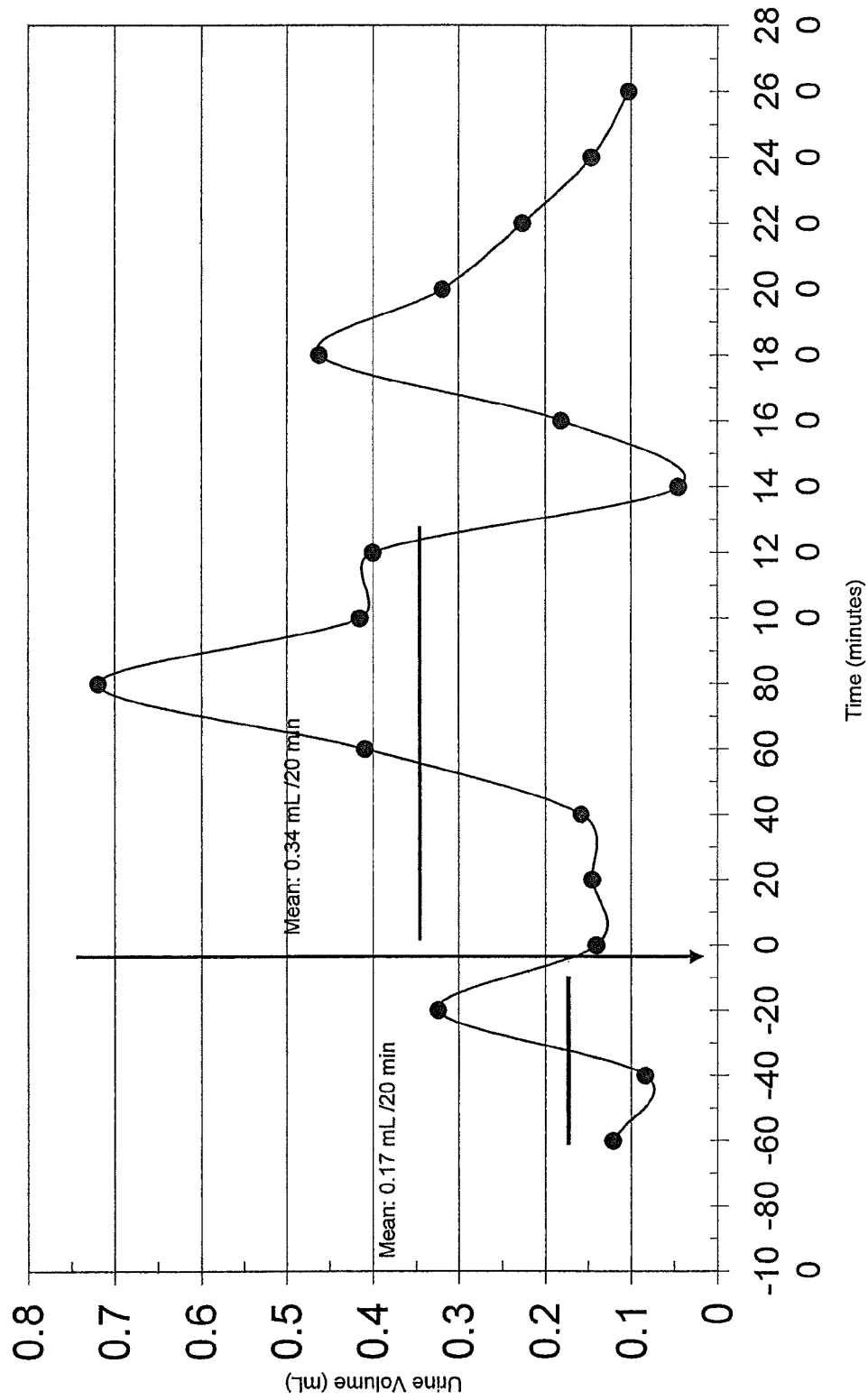
FIG. 24 shows urine volume in response to synthetic xanthurenic acid 8-O-sulfate (20.0 ug) in normal Sprague Dawley rat by oral administration.

Natriuretic Response to Synthetic Xanthurenic Acid 8-O-β-D-glucoside (10 µg i.v.) in a Normal Sprague Dawley Rat A female Sprague Dawley rat (250 g) was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject the test compound. Synthetic xanthurenic acid 8-O-β-D-glucoside, 10 µg i.v. was injected at the time indicated in a 1-mL volume in saline over the course of 10 minutes. At the indicated time the saline infusion was increased tenfold to 0.2 mL/min for ten minutes and returned to 0.02 mL/min for the duration of the assay. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 5-8. Synthetic xanthurenic acid 8-O-β-D-glucoside at 10 µg i.v. caused a sustained natriuretic response in the normal rat. $K^+$ excretion did not increase in response to xanthurenic acid 8-O-β-D-glucoside. The initial natriuretic response in FIG. 6 (10-20 min) was due to the increase in urine volume shown in FIG. 8, and not due to urine $Na^+$ concentration shown in FIG. 7. However by 60-90 minutes after administration the natriuresis was due to the increased urine $Na^+$ concentration as shown in FIG. 7.

Urine production decreased 140 min after administration resulting in decreased natriuresis. However when the saline infusion increased to tenfold to 0.2 mL/min for 10 minutes, $Na^+$ excretion rate increased from 2 uEq/min to 10 uEq/min, seen in FIG. 6. These data are consistent with the idea that xanthurenic acid 8-O-β-D-glucoside inhibited $Na^+$ reabsorption at the distal tubule causing $Na^+$ excretion but only if hydration and GFR were sufficient for enough fluid to reach the distal tubule.

Example 6

Natriuretic Response to Synthetic Xanthurenic Acid 8-O-B-D-glucoside (10 µg) followed by Furosemide (100 µg) in a Normal Sprague Dawley Rat, (Oral Administration)

A female Sprague Dawley rat (250 g) was anesthetized lightly with ether and a urethra catheter was inserted using KY jelly and 2% lidocaine as a lubricant. The rat was restrained in a modified Plexiglas tube so that urine could be collected in 1.5-mL microcentrifuge tubes. No saline infusion was administered. Synthetic xanthurenic acid 8-O-β-D-glucoside was injected with a feeding needle at the time indicated in a 1-mL volume of water over the course of 1 minute. Sixty minutes later 100 µg of furosemide was similarly administered with a feeding needle. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 9-12. Synthetic xanthurenic acid 8-O-β-D-glucoside (10 µg) was orally active by causing a natriuretic response in a normal rat. Sixty minutes after oral administration, furosemide (100 µg) caused sustained $Na^+$ excretion seen in FIGS. 9-11. Pretreatment with xanthurenic acid 8-O-β-D-glucoside followed by furosemide allowed increased $Na^+$ excretion, but did not increase $K^+$ excretion in FIG. 10. Oral furosemide alone caused both $Na^+$ and $K^+$ excretion (data not shown). Pretreatment with xanthurenic acid 8-O-β-D-glucoside inhibited furosemide-induced $K^+$ excretion.

Example 7

Natriuretic Response to Isolated Xanthurenic Acid 8-O-B-D-glucoside (3 µg) followed by Furosemide (20 µg) in Uremic Sprague Dawley Rat (i.v.)

Female Sprague-Dawley rat, weighing 225 g, was made uremic by tying off one kidney and 30-50% of the second kidney. Two weeks later the rat was ready to test for natriuretic activity. The rat was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject isolated xanthurenic acid 8-O-β-glucoside at the time indicated in a 1-mL volume in saline over the course of 10 minutes. After 2 hours 20 ug furosemide was injected in the same manner. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration).

Figure 25:
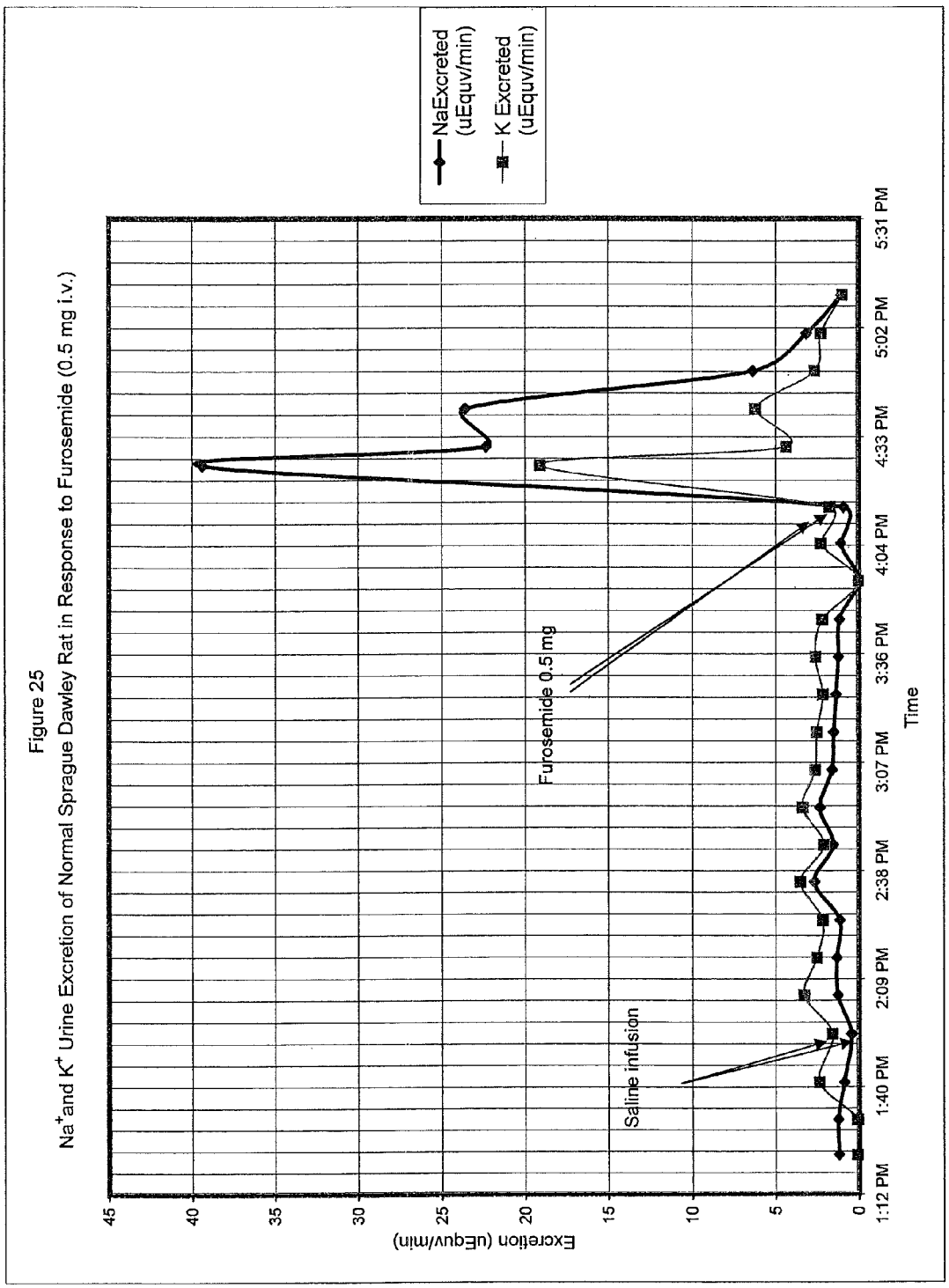
FIG. 25 shows Na$^+$ and K$^+$ urine excretion in normal Sprague Dawley rat in response to furosemide (0.5 mg, i.v.).
Figure 26:
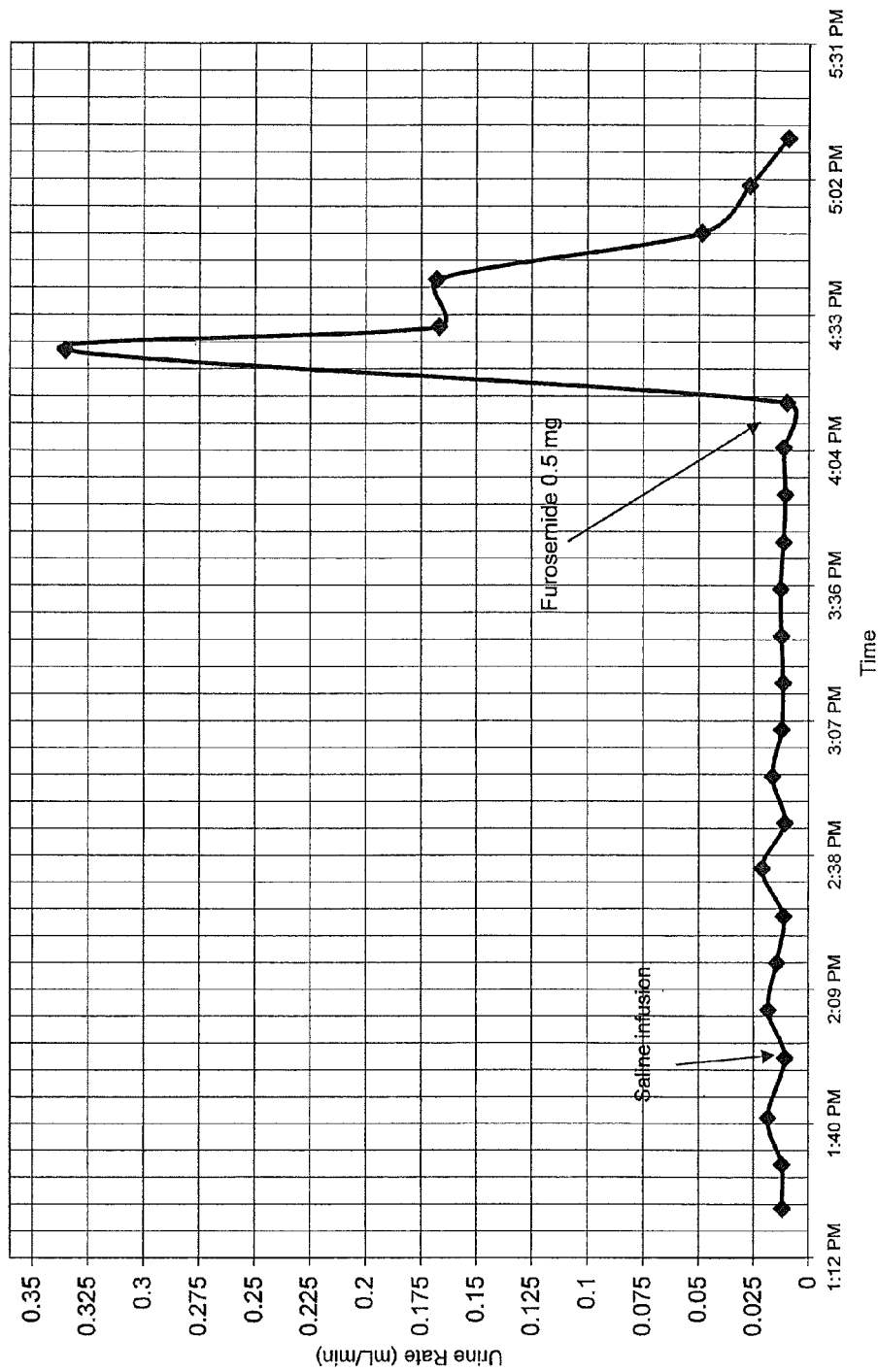
FIG. 26 shows urine excretion rate of normal Sprague Dawley rat in response to furosemide (0.5 mg i.v.).

Results are shown in FIGS. 13-16. Isolated xanthurenic acid 8-O-β-D-glucoside at 3 μg i.v. caused a sustained natriuretic response in the uremic rat. The time course of $Na^+$ excretion peaked at 70 minutes in the uremic rat shown in FIG. 13, which is a similar time course to the synthetic xanthurenic acid 8-O-β-glucoside in the normal rat shown in FIG. 1. $K^+$ excretion in FIGS. 14 and 15 did not increase in response to isolated xanthurenic acid 8-O-β-glucoside. The diuretic response to furosemide was classic in terms of its time course as well as the $Na^+$ excretion. Normally, furosemide also causes $K^+$ excretion to the extent that $K^+$ supplementation is necessary in the clinical use of furosemide. A similar effect in normal rat is illustrated in FIG. 25 (furosemide only). Pretreatment with xanthurenic acid 8-O-β-glucoside followed by furosemide prevented the typical increase in $K^+$ excretion in this assay shown in FIGS. 14 and 15.

Example 8

$Na^+$ and $K^+$ Urine Excretion Response to Isolated Xanthurenic Acid 8-O-sulfate (2.0 μg) in Uremic Sprague Dawley Rat (i.v. Administration)

A female Sprague-Dawley rat, weighing 225 g, was made uremic by tying off one kidney and 30-50% of the second kidney. Two weeks later the rat was ready to test for natriuretic activity. The rat was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject the test compound. Isolated xanthurenic acid 8-O-sulfate, 2 μg, was injected at the time indicated in a 1 mL volume in saline over the course of 10 minutes. Then saline infusion was returned to 0.02 mL/min for the duration of the assay. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration).

Results are shown in FIGS. 17-20. Isolated xanthurenic acid 8-O-sulfate (2 μg, i.v.) caused sustained natriuretic response in the uremic rat. The time course of the natriuresis peaked within 30 minutes and then approached control levels within 70 minutes of treatment, seen in FIGS. 17 and 18. $K^+$ excretion did not increase in response to isolated xanthurenic acid 8-O-sulfate, shown in FIGS. 18 and 19.

Example 9

$Na^+$ and $K^+$ Urine Excretion Response to Synthetic Xanthurenic acid 8-O-sulfate (20 μg) in Normal Sprague Dawley Rat (Oral Administration)

A female Sprague Dawley rat (250 g) was anesthetized lightly with ether and a urethra catheter was inserted using KY jelly and 2% lidocaine as a lubricant. The rat was restrained in a modified Plexiglas tube so that urine could be collected in 1.5-mL microcentrifuge tubes. No saline infusion was administered. Xanthurenic acid 8-O-sulfate was injected with a feeding needle at the time indicated in a 1-mL volume of water over the course of 1 minute. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 21-24. Xanthurenic acid 8-O-sulfate (20 ug) was not orally active with respect to causing a natriuretic response in a normal rat. In particular, the $Na^+$ urine concentration remained below 50 mM in FIG. 21 whereas in i.v. administered xanthurenic acid 8-O-sulfate the $Na^+$ urine concentration increased from 60 mM to 160 mM in FIG. 19. In addition, Xanthurenic acid 8-O-β-D-glucoside was orally active in a normal rat by increasing the $Na^+$ urine concentration to 160 mM in FIG. 11.

Example 10

Protocol for Polyclonal Antibody Production against Xanthurenic Acid 8-O-beta-D-glucoside and Xanthurenic Acid 8-sulfate The following protocol describes the production of polyclonal antibodies to xanthurenic acid 8-O-beta-D-glucoside in the development of an ELISA assay to detect and measure xanthurenic acid 8-O-beta-D-glucoside in urine and plasma. Xanthurenic acid 8-O-beta-D-glucoside is covalently linked to the large protein KLH to elicit an immune response in rabbits. In addition, ASBA is used as a spacer arm (12 Å) between xanthurenic acid 8-O-beta-D-glucoside and KLH. The spacer arm allows better presentation of xanthurenic acid 8-O-beta-D-glucoside in the immune response. In the screening of the antibody response, xanthurenic acid 8-O-beta-D-glucoside is similarly linked to BSA which is then coated onto ELISA wells. The rabbit serum is then screened for xanthurenic acid 8-O-beta-D-glucoside antibodies by incubating the rabbit serum with the BSA conjugated to xanthurenic acid 8-O-beta-D-glucoside. These rabbit antibodies are detected by binding goat-anti-rabbit antibodies that are conjugated to the reporter enzyme horseradish peroxidase (HRP). The substrate, tetramethylbenzidine (TMB) incubates with HRP and the product is measured at 400 nm.

Once the titer of the anti-serum against xanthurenic acid 8-O-beta-D-glucoside is determined, urine samples are tested for the presence of xanthurenic acid 8-O-beta-D-glucoside by competitive ELISA using the specific polyclonal antibody. The validation of xanthurenic acid 8-O-beta-D-glucoside by ELISA will be done by the current HPLC method with fluorescent detection. This HPLC method was initially developed in the isolation of xanthurenic acid 8-O-beta-D-glucoside in human urine. The UV spectrum of xanthurenic acid 8-O-beta- D-glucoside can also be examined in the urine samples. By the current HPLC method, the detection limit of xanthurenic acid 8-O-beta-D-glucoside in urine is 2.7 uM with no solid phase extraction (SPE). SPE is expected to lower HPLC detection limits to nM.

The clinical plasma and urine levels of xanthurenic acid 8-O-beta-D-glucoside and xanthurenic acid 8-sulfate will be established by both ELISA and SPE/HPLC techniques.

What is claimed is:

1. A method for determining xanthurenic acid-8-O-β-D-glucoside present in a human serum sample, comprising:
   a. obtaining a human serum sample; and
   b. measuring the amount of the xanthurenic acid-8-O-β-D-glucoside in the human serum sample.

2. A process for monitoring or detecting a disease associated with an abnormal level of xanthurenic acid-8-O-β-D-glucoside; the process comprising:
   detecting a level of xanthurenic acid-8-O-β-D-glucoside in a biological sample, wherein an elevated level of xanthurenic acid-8-O-β-D-glucoside in the biological sample is associated with the disease.

3. The process of claim 2, wherein said disease is selected from the group consisting of hypertension, edema, acute renal failure, congestive heart failure, chronic renal failure, ascites, increased intra-ocular pressure, nephrotic syndrome or other disease state involving irregularities in fluid/sodium balance.

4. The process of claim 2, wherein said biological sample is a urine sample.

5. The process of claim 2, wherein said biological sample is a serum sample.

6. A method for the chromatographic quantification of xanthurenic acid-8-O-β-D-glucoside in a biological sample, the method comprising:
   a. obtaining a biological sample;
   b. injecting a known volume of the biological sample into the column of an HPLC unit; and
   c. determining the quantity of xanthurenic acid-8-O-β-D-glucoside in the biological sample relative to a standard of xanthurenic acid-8-O-β-D-glucoside.

* * * * *